(12) United States Patent
Adams et al.

(10) Patent No.: US 11,786,650 B2
(45) Date of Patent: Oct. 17, 2023

(54) ASSEMBLIES AND METHODS FOR INFUSION PUMP SYSTEM ADMINISTRATION SETS

(71) Applicant: Smiths Medical ASD, Inc., Plymouth, MN (US)

(72) Inventors: Grant A. Adams, Coon Rapids, MN (US); James Bryan Drost, Woodbury, MN (US); Christopher Allen Lacy, Arden Hills, MN (US); Jonathan Sanborn, St. Louis Park, MN (US); Daniel L. Adamson, Blaine, MN (US); Harshad Borgaonkar, Shoreview, MN (US); Sameer Pai, Plymouth, MN (US); Sean Riley, Minneapolis, MN (US)

(73) Assignee: Smiths Medical ASD, Inc., Plymouth, MN (US)

( * ) Notice: Subject to any disclaimer, the term of this patent is extended or adjusted under 35 U.S.C. 154(b) by 95 days.

(21) Appl. No.: 17/498,449

(22) Filed: Oct. 11, 2021

(65) Prior Publication Data
US 2022/0096737 A1  Mar. 31, 2022

Related U.S. Application Data

(63) Continuation of application No. 16/309,909, filed as application No. PCT/US2017/037929 on Jun. 16, 2017, now Pat. No. 11,167,081.

(60) Provisional application No. 62/350,905, filed on Jun. 16, 2016.

(51) Int. Cl.
*A61M 5/142* (2006.01)
*A61M 39/28* (2006.01)

(52) U.S. Cl.
CPC ...... *A61M 5/14228* (2013.01); *A61M 39/284* (2013.01); *A61M 2205/3306* (2013.01); *A61M 2205/3584* (2013.01); *A61M 2205/50* (2013.01); *A61M 2205/6054* (2013.01); *A61M 2205/6081* (2013.01)

(58) Field of Classification Search
CPC .. A61M 5/14228; A61M 5/142; A61M 5/168; A61M 39/284; A61M 39/287; A61M 2205/3306; A61M 2205/6054; A61M 2205/6063
See application file for complete search history.

(56) References Cited

U.S. PATENT DOCUMENTS 5,478,211 A * 12/1995 Dominiak ........... A61M 39/281
607/153

* cited by examiner

*Primary Examiner* — Tasnim Mehjabin Ahmed
(74) *Attorney, Agent, or Firm* — Patterson Thuente IP

(57) ABSTRACT

An assembly is configured to position a peristaltic tube with respect to a linear peristaltic pump drive of an infusion pump. The assembly can include a peristaltic tube, first and second tube couplers, a frame, first and second securement plates, a free-flow prevention arm, and a biasing mechanism. The frame can include a snap-fit tab configured to releasably secure the assembly to an assembly receptacle of the infusion pump. The free-flow prevention arm can be selectively movable between a free-flow preventing position and a free-flow allowing position. A latching mechanism can be ergonomically manipulable to latch the free-flow prevention arm in a free-flow allowing position, and to unlatch the free-flow prevention arm such that the biasing mechanism is able to bias the free-flow prevention arm to the free-flow preventing position.

20 Claims, 17 Drawing Sheets

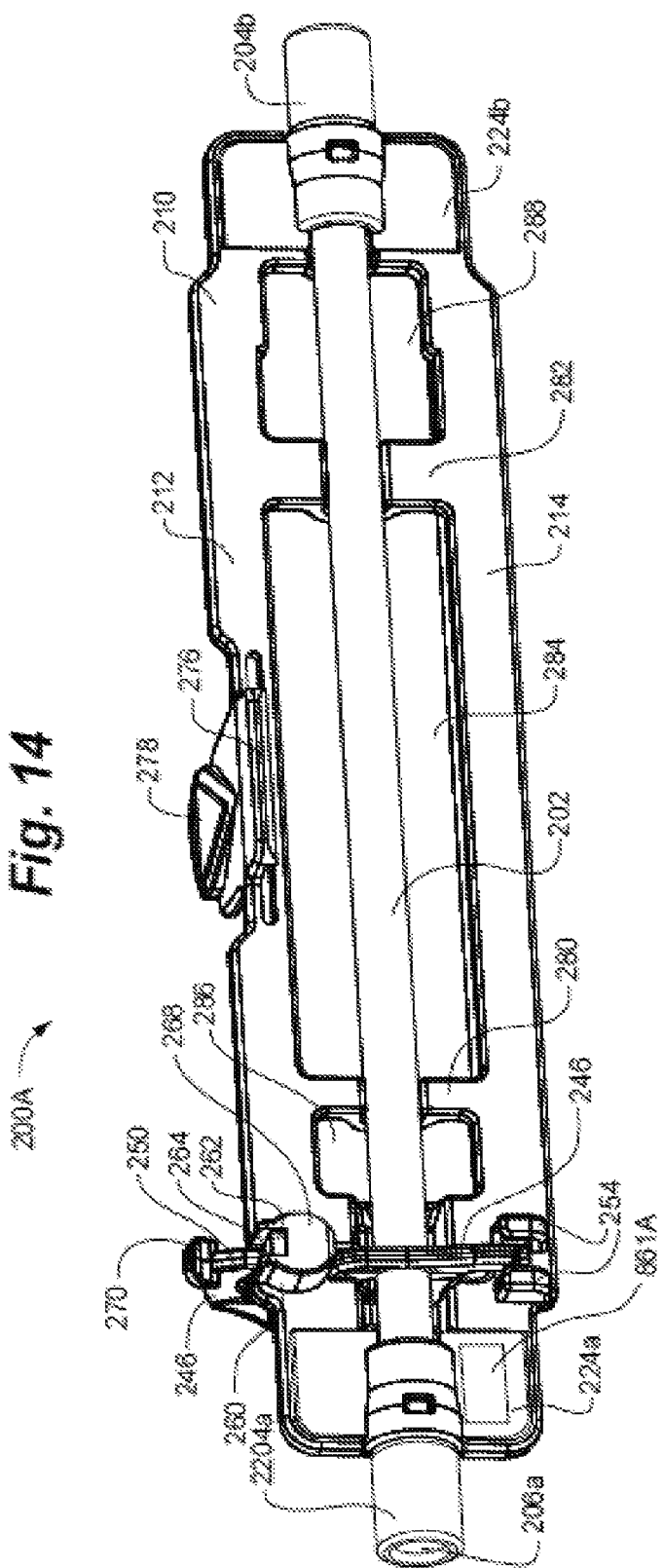

ASSEMBLIES AND METHODS FOR INFUSION PUMP SYSTEM ADMINISTRATION SETS

RELATED APPLICATION

This application is a continuation of U.S. application Ser. No. 16/309,909 filed Dec. 13, 2018, which is a National Phase entry of PCT Application No. PCT/US2017/037929 filed Jun. 16, 20217, which claims the benefit of U.S. Provisional Application No. 62/350,905, filed on Jun. 16, 2016, which are hereby fully incorporated herein by reference.

TECHNICAL FIELD

This disclosure relates to infusion pump systems, and more particularly, to assemblies and methods for infusion pump system administration sets.

BACKGROUND

Infusion pumps are useful medical devices for managing the delivery and dispensation of many types of therapeutic infusates. Infusion pumps provide significant advantages over manual administration by accurately delivering infusates over an extended period of time. Infusion pumps are particularly useful for treating diseases and disorders that require regular pharmacological intervention, including cancer, diabetes, and vascular, neurological, and metabolic disorders. They also enhance the ability of healthcare providers to deliver anesthesia and manage pain. Infusion pumps are used in various settings, including hospitals, nursing homes, and other short-term and long-term medical facilities, as well as in residential care settings. There are many types of infusion pumps, including ambulatory, large volume, patient-controlled analgesia (PCA), elastomeric, syringe, enteral, and insulin pumps. Infusion pumps can be used to administer medication through various delivery methods, including intravenously, intraperitoneally, intra-arterially, intradermally, subcutaneously, in close proximity to nerves, and into an intraoperative site, epidural space or subarachnoid space.

In a particular type of infusion pump system that is commonly referred to as a "peristaltic" pump system, delivery of an infusate to a patient is typically accomplished with the use of an infusion administration set, that is typically disposable after use and can provide a fluidic pathway (e.g., tubing) for the infusate from a reservoir (such as an intravenous or "IV" bag) to a patient, in cooperation with a pump that controls a rate of flow of the infusate. Peristaltic infusion pumps typically incorporate a peristaltic pumping mechanism that can function by repetitively occluding successive sections of tubing of the administration set in a wave-like motion. For a peristaltic pumping mechanism to work as intended, proper positioning should be maintained between the portion of tubing (or other element) of the administration set and the elements of the peristaltic pumping mechanism that interact with the administration set. In addition, the pump may include devices such as occlusion sensors and air-in-line detectors that may require correct placement of the administration set in or with the pump. A practical peristaltic infusion pump system generally includes a means, method, and/or mechanism by which infusion administration sets (that are typically disposable, as aforementioned) can be properly engaged with the pump before infusate delivery is commenced and then disengaged from the pump after infusate delivery is performed or completed. It is also to be noted that a so-called "large volume pump" or "LVP" system typically includes a peristaltic pump and related components as aforedescribed. It is further to be noted that in some publications the term "volumetric pump" may also be variously used to refer to, whether correctly or incorrectly, a peristaltic pump or a large volume pump.

Infusion administration sets preferably include, and may even be required by law or regulation to include, mechanisms to preclude uncontrolled free-flow of infusate when not engaged with a pump. Such "flow stop" devices may default to or be biased in a free-flow preventing mode or state when the administration set is not engaged with the pump. When engaged with the pump, there generally needs to be a mechanism to disengage or otherwise act on the flow stop device so that the pump can deliver infusate. Further, it may be desirable to allow for manual over-ride of the flow stop device for functions such as priming and/or intentional gravity-fed infusate delivery, when the administration set is not engaged with the pump.

In view of the multiple functional objectives for infusion administration sets, there is a desire for improved, easy-to-use administration sets that reduce burdens on caregivers and increase patient safety.

SUMMARY

This disclosure relates to infusion pump systems, and more particularly, to assemblies and methods for infusion pump system administration sets.

In an illustrative but non-limiting example, the disclosure provides an assembly configured to position a peristaltic tube with respect to a linear peristaltic pump drive of an infusion pump. The assembly can include a peristaltic tube, first and second tube couplers, a frame, first and second securement plates, a free-flow prevention arm, and a biasing mechanism.

The peristaltic tube can be formed of a resilient material and can be suitable for compression by the linear peristaltic pump drive of the pump. The first and second tube couplers can be attached at opposing ends of the peristaltic tube, with each of the first and second tube couplers having a lumen in fluidic communication with the peristaltic tube.

The frame can include a first beam and a second beam substantially parallel to the first beam, the first and second beams substantially lying in a first plane. In some cases, at least one of the first and second beams can be substantially L-shaped. The frame also can include a first end plate joining the first and second beams at a first end, and a second end plate joining the first and second beams at a second end, with the first and second end plates substantially lying in the first plane. The first beam can include a snap-fit tab projecting away from the first plane in a first direction and a snap release handle operatively coupled to the snap-fit tab. The snap-fit tab can be configured to releasably secure the assembly to an assembly receptacle of the infusion pump, such that when the assembly is secured via the snap-fit tab to the assembly receptacle, the peristaltic tube is positioned for engagement with the linear peristaltic pump drive of the pump. A defined manipulation of the snap release handle can release the snap-fit tab and therefore the assembly from the assembly receptacle.

The assembly can also include a first securement plate configured to cooperate with the first end plate to couple the first tube coupler to the frame, and a second securement plate configured to cooperate with the second end plate to couple the second tube coupler to the frame.

The assembly can include a free-flow prevention arm coupled to the frame at an arm end and having a latching structure configured to cooperate with a latching receiver of the frame, such that the latching structure and the latching receiver together provide a latching mechanism. The free-flow prevention arm can be selectively movable between a free-flow preventing position and a free-flow allowing position. In the free-flow preventing position, the free-flow prevention arm and the frame can squeezingly occlude the peristaltic tube; in the free-flow allowing position, the free-flow prevention arm and the frame can be relatively positioned to allow the peristaltic tube to pass therebetween such that the peristaltic tube is not squeezingly occluded. The latching mechanism can be ergonomically manipulable to latch the free-flow prevention arm in a free-flow allowing position. The biasing mechanism of the assembly can be configured to bias the free-flow prevention arm to the free-flow preventing position. The latching mechanism of the assembly can be ergonomically manipulable to unlatch the free-flow prevention arm such that the biasing mechanism is able to bias the free-flow prevention arm to the free-flow preventing position.

In some instances, the latching structure of the free-flow prevention arm can include a thumb press surface and latching receiver of the frame can include a finger press surface.

In some cases, the latching structure of the free-flow prevention arm can include a release catch. The release catch of the latching structure of the free-flow prevention arm can be structured to provide a surface for a human finger to flex the free-flow prevention arm sufficiently to unlatch the latching mechanism. The release catch of the latching structure of the free-flow prevention arm can be structured to cooperate with at least one ramp in the assembly receptacle of the infusion pump so that when the assembly is secured to the assembly receptacle, the release catch slides along the ramp(s) as the free-flow prevention arm is moved toward the free-flow allowing position, such that force exerted on the release catch by the ramp(s) flexes the free-flow prevention arm sufficiently to prevent the latching mechanism from latching in the free-flow allowing position. Alternatively or in addition, the release catch of the latching structure of the free-flow prevention arm can be structured to cooperate with at least one ramp in the assembly receptacle of the infusion pump such that if, before the assembly is secured to the assembly receptacle, the latching mechanism is latched in the free-flow allowing position, then subsequently when the assembly is secured to the assembly receptacle via the snap-fit tab, the ramp(s) exerts force on the release catch adequate to flex the free-flow prevention arm sufficiently that the latching mechanism is released.

In some cases, the biasing mechanism can include a spring formed separately from the frame and from the free-flow protection arm, the spring being captured between the frame and the free-flow protection arm.

In some cases, the free-flow prevention arm can be hingedly coupled to the frame at the arm end. In some such instances, the free-flow prevention arm can be hingedly coupled to the frame at the arm end via a hinge mechanism that substantially does not impart torque between the free-flow prevention arm and the frame.

In some cases, the latching mechanism can be ergonomically manipulable with a single hand to latch the free-flow prevention arm in the free-flow allowing position.

In some cases, the latching mechanism can be ergonomically manipulable with a single hand to unlatch the free-flow prevention arm such that the biasing mechanism is able to bias the free-flow prevention arm to the free-flow preventing position.

In some instances, the frame can define a slot transverse to the peristaltic tube and generally aligned with the free-flow prevention arm, such that when the free-flow prevention arm is in the free-flow preventing position, the free-flow prevention arm can press the peristaltic tube at least partially into the slot. In some such instances, the frame can include a buttress spanning the slot, with the buttress generally aligned with the peristaltic tube. The buttress can provide a guard against accidental latching of the latching mechanism.

In some cases, the assembly can include an identifier containing information related to a particular route of infusion associated with the assembly. In some cases, the identifier is a colored surface or tag providing an associated visible or infrared optical wavelength for detection. In other cases, the identifier includes at least one of: an RFID tag, a magnetic key, an identifying pin configuration or a protrusion of identifying size and shape.

In another illustrative but non-limiting example, the disclosure provides an infusion pump system that includes an infusion pump that has assembly receptacle, and a disposable assembly configured to position a peristaltic tube with respect to a linear peristaltic pump drive of the infusion pump. The disposable assembly can be structured and configured substantially as aforedescribed in the first illustrative but non-limiting example of this Summary.

In some cases, the assembly receptacle can define at least one ramp, and the release catch of the latching structure of the free-flow prevention arm can be structured to cooperate with the ramp(s) in the assembly receptacle of the infusion pump so that when the assembly is secured to the assembly receptacle, the release catch slides along the ramp(s) as the free-flow prevention arm is moved toward the free-flow allowing position, such that force exerted on the release catch by the ramp(s) flexes the free-flow prevention arm sufficiently to prevent the latching mechanism from latching in the free-flow allowing position.

In some cases, the infusion pump can further include a receptacle door that can open and close to allow or block access to the assembly receptacle. The receptacle door can include a free-flow protection arm pusher and a door latch lever that are operatively coupled such that when the assembly is received by the assembly receptacle and the receptacle door is closed, the free-flow protection arm pusher can push the free-flow protection arm from the free-flow preventing position to the free-flow allowing position as the door latch lever is moved from an unlatched position to a latched position.

In some cases, a system includes an infusion pump having an assembly receptacle and a disposable assembly. The assembly receptacle includes a sensing device that detects route of infusion information from an identifier on the assembly. In certain cases, the sensing device is an optical sensor. In other cases, the sensing device includes at least one of: an RFID reader, a magnetic key reader, and a pin identifier.

In yet another illustrative but non-limiting example, the disclosure provides an assembly configured to position a peristaltic tube with respect to a linear peristaltic pump drive of an infusion pump. The assembly can include a peristaltic tube, a frame, first and second tube supports, and a free-flow prevention arm.

The peristaltic tube can be formed of a resilient material and can be suitable for compression by the linear peristaltic pump drive of the pump.

The frame can include a beam and a latching receiver.

The first tube support can be positioned at a first end of the beam of the frame, and the second tube support positioned at a second end of the beam of the frame. The first tube support and the second tube support can be configured to maintain the position of the peristaltic tube with respect to the frame.

The free-flow prevention arm can be attached to the frame at an arm end and can have a latching structure configured to cooperate with the latching receiver of the frame, such that the latching structure and latching receiver together providing a latching mechanism. The free-flow prevention arm can be movable between a free-flow preventing position and a free-flow allowing position. In the free-flow preventing position, the free-flow prevention arm and the frame can squeezingly occlude the peristaltic tube, and in the free-flow allowing position, the free-flow prevention arm and the frame can allow the peristaltic tube to pass therebetween such that the peristaltic tube is not occluded. The latching mechanism, in a latched state, can constrain the free-flow prevention arm to the free-flow allowing position. In an unlatched state, the latching mechanism may not constrain the free-flow prevention arm to the free-flow allowing position. The latching mechanism can be manipulable with a single hand to move to the latched state, and can further be manipulable with a single hand to move to the unlatched state.

In some cases, the beam can include a snap-fit tab projecting away from the beam, and can also include a snap release handle operatively coupled to the snap-fit tab. The snap-fit tab can be configured to releasebly secure the assembly to an assembly receptacle of the infusion pump. When the assembly is secured via the snap-fit tab to the assembly receptacle, the peristaltic tube can be positioned for engagement with the linear peristaltic pump drive. Manipulation of the snap release handle can release the snap-fit tab and thereby the assembly from the assembly receptacle.

In some cases, the assembly can be configured to releasably secure to an assembly receptacle of the infusion pump. The latching structure of the free-flow prevention arm can include a release catch structured to provide purchase for a human finger to flex the free-flow prevention arm sufficiently to unlatch the latching mechanism. The release catch of the latching structure of the free-flow prevention arm can be structured to cooperate with at least one ramp in the assembly receptacle of the infusion pump such that if, before the assembly is secured to the assembly receptacle, the latching mechanism is latched in the free-flow allowing position, then subsequently when the assembly is secured to the assembly receptacle, the ramp(s) can exert force on the release catch adequate to flex the free-flow prevention arm sufficiently that the latching mechanism is released.

In another illustrative but non-limiting example, the disclosure provides an assembly configured to position a peristaltic tube with respect to a linear peristaltic pump drive of an infusion pump. The assembly includes a peristaltic tube, a first tube and second tube couplers, a frame, a free-flow prevention arm, and a biasing mechanism. The peristaltic tube is suitable for compression by the linear peristaltic pump drive. The first tube coupler and the second tube coupler are each attached at opposing ends of the peristaltic tube. The first tube coupler and the second tube coupler each have a lumen in fluidic communication with the peristaltic tube. The frame is coupled to the first tube coupler and the second tube coupler at spaced-apart locations. The frame is configured for releasable attachment to the infusion pump such that the peristaltic tube is positioned for engagement with the linear peristaltic pump drive. The frame further includes a latching receiver projecting from the frame having a finger press surface. The free-flow prevention arm is hingedly coupled to the frame at an arm end and has a latching structure sized to cooperate with the latching receiver. The latching structure includes a thumb press surface projecting outwardly from the arm, and a release catch disposed at a spaced-apart location from the thumb press surface. The finger press surface of the latching receiver and the thumb press surface of the latching structure are oppositely-disposed and operatively coupled in close proximity for ergonomic manipulation with a single hand to selectively latch and unlatch the latching receiver of the free-flow prevention arm between a free-flow preventing position and a free-flow allowing position. The biasing mechanism is located between the frame and the free-flow protection arm, configured to bias the free-flow prevention arm to the free-flow preventing position.

In some cases, the frame includes a snap-fit tab and a snap release handle. In some cases, the frame includes an identifier containing information related to a route of infusion associated with the assembly. In some cases, the identifier is a colored surface or tag providing an associated visible or infrared optical wavelength for detection. In some cases, the identifier contains at least one of: an RFID tag, a magnetic key, an identifying pin configuration, and an identifying protrusion.

The above summary is not intended to describe each and every example or every implementation of the disclosure. The Description that follows more particularly exemplifies various illustrative embodiments.

BRIEF DESCRIPTION OF THE FIGURES

The following description should be read with reference to the drawings. The drawings, which are not necessarily to scale, depict examples and are not intended to limit the scope of the disclosure. The disclosure may be more completely understood in consideration of the following description with respect to various examples in connection with the accompanying drawings, in which:

FIG. 14 is an alternative embodiment of a back schematic perspective view of the assembly of FIG. 2;

DESCRIPTION

The following description should be read with reference to the drawings, in which like elements in different drawings may be numbered in like fashion. The drawings, which are not necessarily to scale, depict selected examples and are not intended to limit the scope of the disclosure. Although examples of construction, dimensions, and materials may be illustrated for the various elements, those skilled in the art will recognize that many of the examples provided have suitable alternatives that may be utilized.

Figure 1:
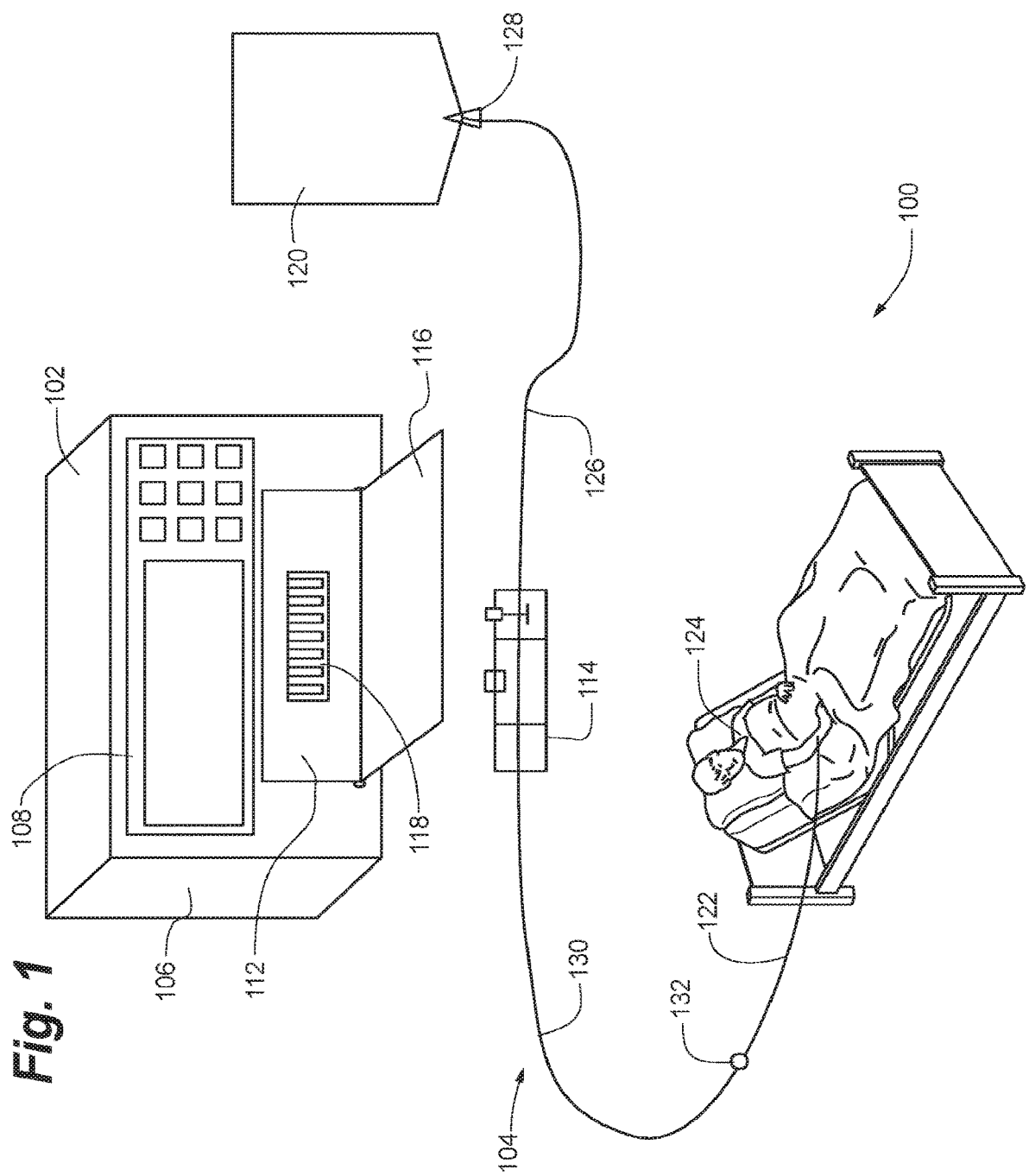
FIG. 1 is a schematic perspective view of an example embodiment of a peristaltic infusion pump system that includes a peristaltic pump and administration set.

FIG. 1 is a schematic perspective view of an example embodiment of a peristaltic infusion pump system 100 that includes a peristaltic pump 102 and a disposable administration set 104 that is structured and configured to operatively couple to pump 102. In FIG. 1, administration set 104 is illustrated as not coupled to pump 102.

Pump 102 can include a housing 106 and a user interface 108 (that can include, for example, a display screen, keypad, audio speaker, and any other suitable user interface components) for prompting and/or relaying commands to a control system or controller (not illustrated) of pump 102, and/or for communicating from/to the controller to/from users. User interface 108 generally can allow a user to enter various parameters, including but not limited to names, drug information, limits, delivery shapes, information relating to hospital facilities, as well as various user-specific parameters (e.g., patient age and/or weight) along with so-called "five rights" verification or inputs. Pump 102 can include any appropriate wired or wireless input/output (I/O) interface port and/or protocol (including, but not limited to, USB, Ethernet, WiFi, NFC, Bluetooth, ZigBee, IrDA, and the like) for connecting pump 102 to a network or computer (not illustrated) having software designed to interface with pump 102.

User inputs to pump 102 can be provided by programming from an authorized user, such as a patient, pharmacist, scientist, drug program designer, medical engineer, nurse, physician, or other authorized medical practitioner or healthcare provider. User inputs may utilize direct interfacing (via, e.g., keyboards, touch screens, or other touch-based inputs) as shown, and/or user inputs may utilize indirect or "touchless" interfacing (i.e., gestures; voice commands; facial movements or expressions; finger, hand, head, body and arm movements; or other inputs that do not require physical contact such as cameras, sensors of electric field, capacitance, or sound). User inputs generally can be interfaced, communicated, sensed, and/or received by operator input mechanisms of user interface 108.

In the present disclosure, a controller of a pump can be any suitable controller, microcontroller, microprocessor, or the like. Such a controller can include and/or be operatively coupled to any other hardware or software resource needed for its function, such as any suitable memory of any suitable capacity, containing any suitable software, firmware, operating parameters, and so on. The controller can be configured and programmed to execute, command, and/or perform any suitable actions, tasks, steps, and/or methods for controlling the pump. The pump can include a plurality of physically and/or logically distinct controllers, such as application-specific processors. In the present disclosure, a plurality of such controllers of a pump may be referred to collectively in the singular as the controller of the pump. As mentioned elsewhere herein, methods of the present disclosure can be implemented by the controller of a pump, and/or in some instances by another controller, such as by a controller of another pump, a system of pumps, a controller implemented on a server, or any other appropriate controller. As such, any reference in the present disclosure to a controller in the singular should not be interpreted as strictly limiting to a single physical or logical controller (unless explicitly limited to a single controller), but rather, can include systems and/or methods in which controller functions are provided by one or more controllers.

Power to infusion pump 102 can be provided via an AC or DC power cord or from an internally provided battery source (not illustrated), or by any other suitable means. Embodiments can also include a wireless power source (not illustrated).

Pump 102 can include an assembly receptacle 112 configured to receive an assembly 114 of the administration set 104, and a receptacle door 116 that can open and close to allow or block access to assembly receptacle 112. Tube-engaging members 118 of a linear peristaltic pump drive can be located in assembly receptacle 112. As discussed in further detail herein, assembly 114 of administration set 104 can be configured and structured to position elements of set 104 in an operative relationship with the linear peristaltic pump drive, including tube-engaging members 118.

Administration set 104 can provide a fluidic pathway from an IV bag 120 or other infusate reservoir to an infusion set 122 that ultimately delivers infusate(s) to a patient 124. It is to be appreciated and understood that, although the present disclosure refers to an IV bag 120 or other infusate reservoir and an administration set 104 (thereby implying only one reservoir, one infusate substance, and one administration set), subject matter hereof could include or be applicable to a plurality of same, similar, or different infusate reservoirs, infusates, and administration sets. Administration set 104 can include, in addition to assembly 114, upstream tubing 126 that can extend from IV bag 120 or other reservoir to assembly 114. Upstream tubing 126 can terminate in a bag spike 128 or other connector. Administration set 104 can also include downstream tubing 130 that can extend from assembly 114 to infusion set 122. Downstream tubing 130 can be fluidically coupled to infusion set 122 or other catheter with connector 132 such as a Luer-type connector or any other suitable connector, such as one of those contemplated, specified, defined, or described by one of the ISO 80369 series of small bore connector standards.

Figure 2:
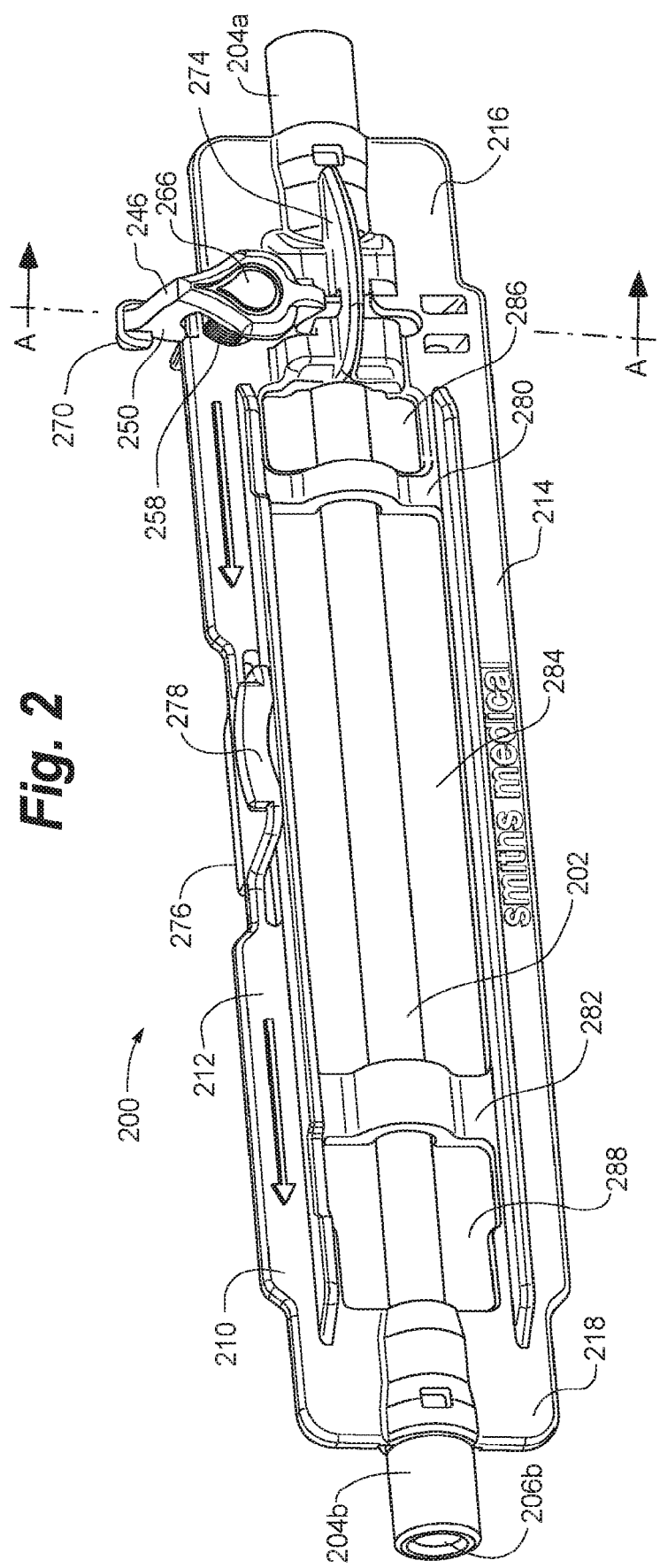
FIG. 2 is a front schematic perspective view of an example assembly of the administration set of FIG. 1.
Figure 3:
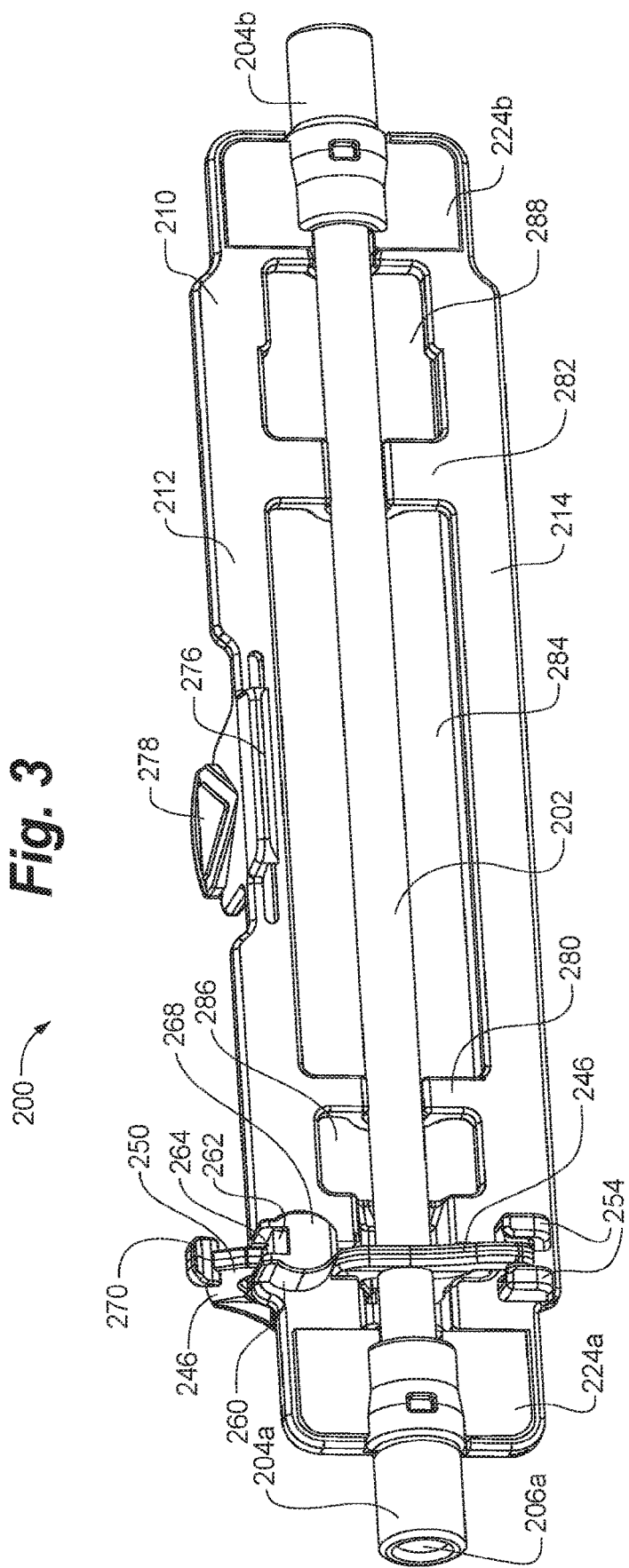
FIG. 3 is a back schematic perspective view of the assembly of FIG. 2.
Figure 4:
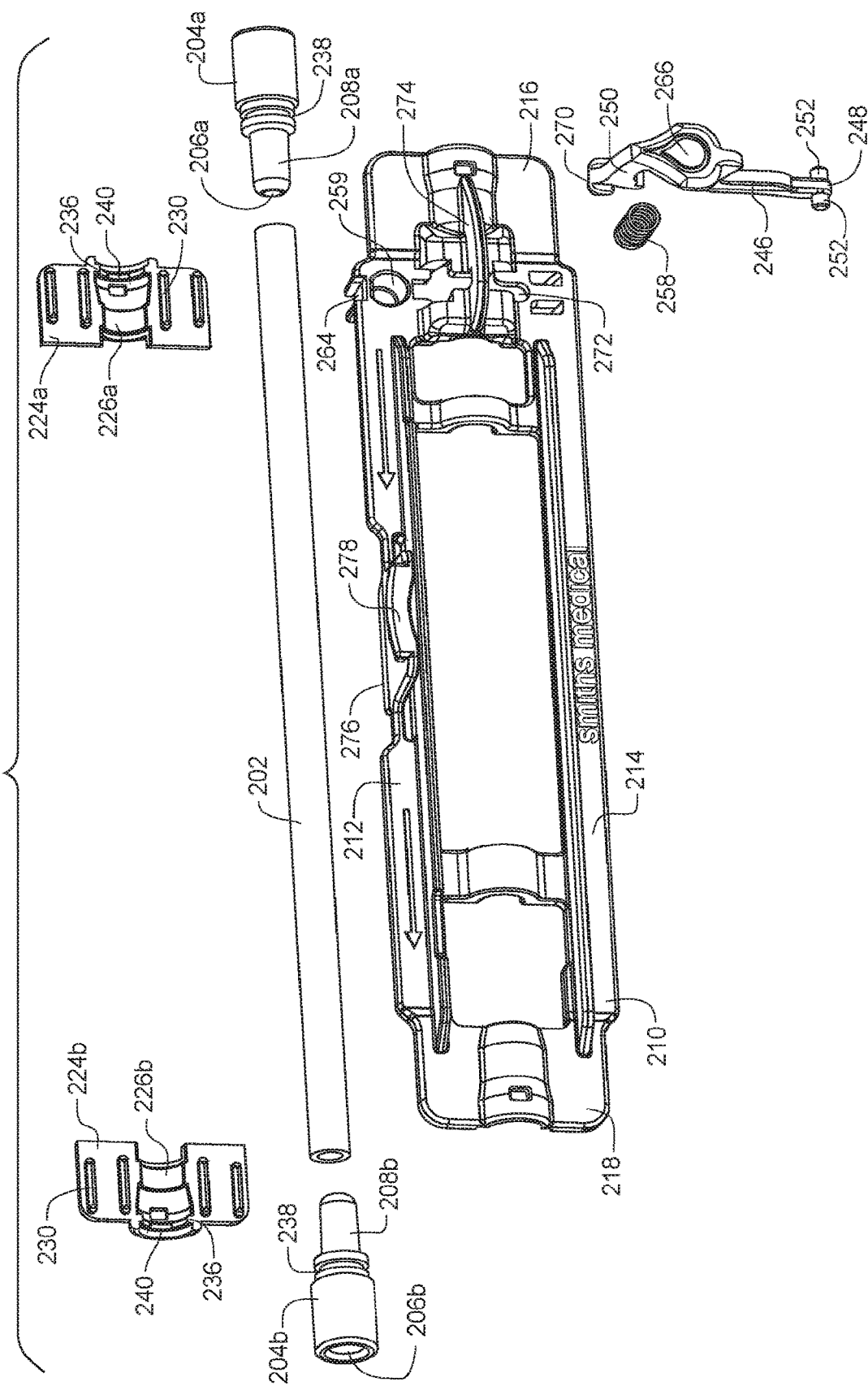
FIG. 4 is a front schematic perspective exploded view of the assembly of FIG. 2.
Figure 5:
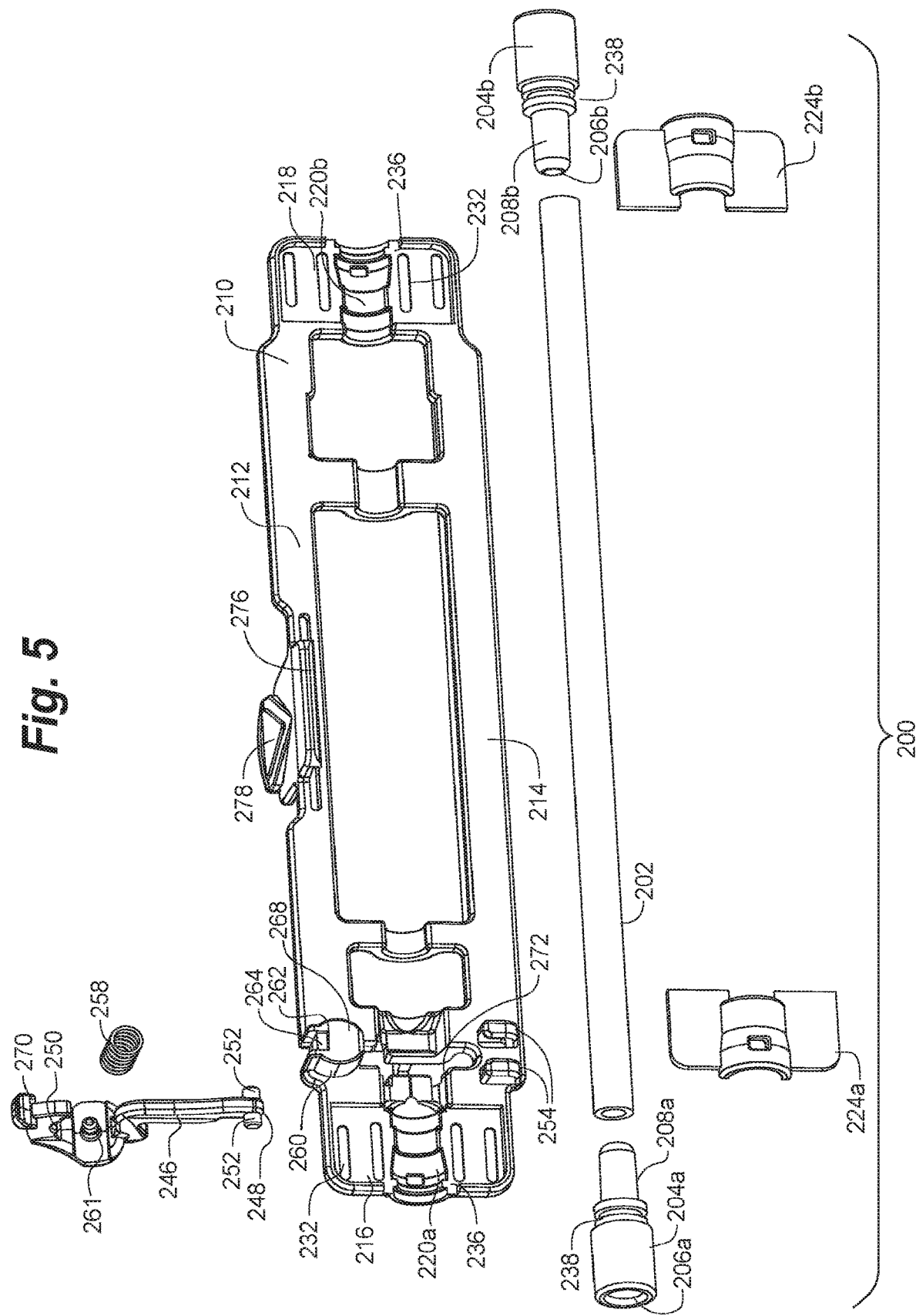
FIG. 5 is a back schematic perspective exploded view of the assembly of FIG. 2.

FIGS. 2 and 3 are front and back schematic perspective views, respectively, of an example assembly 200, which can be assembly 114 of administration set 104 of FIG. 1. FIGS. 4 and 5 are front and back schematic perspective exploded views, respectively, of assembly 200. The adjectives "front" and "back" are used in relation to the orientation of assembly 200 when received by assembly receptacle 112 of pump 102, with the back side of the assembly facing inwardly toward the pump, and the front side of the assembly facing outwardly away from the pump. Elsewhere in this disclosure, descriptors such as "top," "upper," "bottom," and "lower" may be used, which those of ordinary skill will recognize in relation to the normal orientation of system 100 and assembly 200 with respect to the surface of the earth. In most or all Figures of the present disclosure, assembly 114 and components thereof are illustrated oriented with their top or upper portions toward the top sides of the pages on which they are printed or rendered.

Assembly 200 can include a peristaltic tube 202 formed of a resilient material that is suitable for compression (and recovery from compression) by the linear peristaltic pump drive of pump 102. In some embodiments, peristaltic tube 202 is formed from silicone. In other embodiments, polyvinyl chloride, polyurethane, latex rubber, or any other suitable compressible resilient material can be used. At opposing ends of peristaltic tube 202, assembly 200 can include first and second tube couplers 204a, 204b. Tube couplers 204a and 204b can be identical in structure, as in the illustrated example embodiment of assembly 200, but in some embodiments tube couplers may not be identical. Tube couplers 204a, 204b can function to fluidically couple the peristaltic tube 202 with upstream tubing 126 and downstream tubing 130 illustrated in FIG. 1 (but not illustrated in FIGS. 2-5 and 8-11), respectively. Tube couplers 204a, 204b can include lumens 206a, 206b (as illustrated, e.g., in FIGS. 3 and 2, respectively) that can be in fluidic communication with peristaltic tube 202 and/or upstream tubing 126 and downstream tubing 130, respectively, when the corresponding tube coupler is coupled to the corresponding tube/tubing. Note that in the example embodiment of assembly 200, tube coupler 204a can be coupled to upstream tubing 126 and tube coupler 204b can coupled to downstream tubing 130, but this is not limiting and in some embodiments the coupling correspondence could be reversed.

Tube couplers 204a, 204b can be manufactured or formed from, or otherwise include, any suitable material or materials. In some embodiments, tube couplers 204a, 204b can be formed from acrylonitrile butadiene styrene (ABS). In other embodiments, polycarbonate, polyester, polypropylene, polyvinyl chloride or any other suitable semi-rigid material can be used.

Tube couplers 204a, 204b can include peristaltic tube receiving portions 208a, 208b as illustrated in FIG. 4, dimensioned to receive and engage interior surfaces of peristaltic tube 202 by way of a friction fit in each. Peristaltic tube 202 may be stretched or otherwise expanded in order to fit around peristaltic tube receiving portions 208a, 208b. The fit between peristaltic tube 202 and peristaltic tube receiving portions 208a, 208b can result in a fluidic seal between the tube 202 and tube coupler 204a, 204b. Relative dimensions of the peristaltic tube 202 and peristaltic tube receiving portions 208a, 208b can be selected to affect such sealing. In some embodiments, an adhesive or other bonding agent can be used for attaching peristaltic tube 202 and peristaltic tube receiving portions 208a, 208b, but this is not required. In some embodiments, a swelling or lubricating agent may be used during assembly. Opposite peristaltic tube receiving portions 208a, 208b, lumens 206a, 206b can be dimensioned to receive upstream tubing 126 and downstream tubing 130, where the couplers and tubing can be adhered or otherwise bonded. These ways for providing coupling between tube couplers 204a, 204b and peristaltic tube 202 and/or upstream tubing 126 and downstream tubing 130 should not be construed as limiting, and in other embodiments other arrangements and variations are possible.

As illustrated in FIGS. 2-5, assembly 200 can include a frame 210 configured to receive tube couplers 204a, 204b and thereby substantially hold peristaltic tube 202 when coupled to the tube couplers, in a substantially defined position relative to frame 210. Frame 210 can include a first beam 212 and can also include a second beam 214 that is substantially parallel to first beam 212. The substantially parallel first beam 212 and second beam 214 can lie substantially in, or define, a first plane (not illustrated). In this non-limiting example, either or both beams 212, 214 can be "L" shaped, as illustrated, although this is not required in all embodiments. When "L" shaped, one leg of the "L" can lie in the first plane, and the other leg of the "L" can be perpendicular to the first plane.

At a first end, frame 210 can include a first end plate 216 joining first and second beams 212, 214, with first end plate 216 substantially lying in the first plane of first and second beams. 212, 214. At a second end, frame 210 can include a second end plate 218 joining first and second beams 212, 214, with second end plate 218 substantially lying in the first plane of first and second beams 212, 214. First end plate 216 and second end plate 218 can each define a channel 220a, 220b (respectively; visible, for example, in FIG. 5) configured to receive corresponding tube coupler 204a, 204b.

Corresponding to first end plate 216 and second end plate 218, assembly 200 can include a first securement plate 224a and a second securement plate 224b respectively, that are structured and configured to cooperate with end plates 216, 218 to couple tube couplers 204a, 204b to frame 210. Similarly to first and second end plates 216, 218, first and second securement plates 224a, 224b can each define a channel 226a, 226b (respectively; visible, for example, in FIG. 4) configured to receive corresponding tube coupler 204a, 204b.

Frame 210 (including end plates 216, 218) and securement plates 224a and 224b, can be manufactured or formed from, or otherwise include, any suitable material or materials. In some embodiments, these components can be formed from acrylonitrile butadiene styrene (ABS). In other embodiments, polycarbonate, polyester, polypropylene, polyvinyl chloride or any other suitable semi-rigid material can be used.

First and second end plates 216, 218 can be mated to first and second securement plates 224a, 224b, respectively, with first and second tube couplers 204a, 204b positioned or held (or colloquially, "sandwiched") between each mated corresponding pair of end plates and securment plates. Any suitable structures and/or means can be used to hold the pairs of end and securement plates together when mated. In illustrated example assembly 200, end plates 216, 218 and securement plates 224a, 224b, can be respectively joined by ultrasonic welding. End plates 216, 218 and securement plates 224a, 224b can be structured and configured with features to facilitate ultrasonic welding. For example, securement plates 224a, 224b can include bars 230 (visible in FIG. 4) that can include ultrasonic welding energy directors, and end plates 216, 218 can include slots 232 (visible in FIG. 5) dimensioned and positioned to receive the bars 230. As illustrated in this example of assembly 200, each securement plate 224a, 224b includes four bars 230 that are substantially identical in shape, and each end plate 216, 218 includes four slots 232 also substantially identical in shape, but it is not necessary for all bars and slots to have the same shapes, nor is the quantity of four bars/slots required for each pair of plates. Variations in number, location, and shapes of ultrasonic welding components are possible. In some embodiments, asymmetries in ultrasonic welding components could be used to prevent mis-oriented (e.g., upside-down, reversed, etc.) attachment of securement plates 224a, 224b to end plates 216, 218. In some embodiments, including that of FIGS. 2, 3, 4, and 5, securement plates 224a, 224b can have essentially the same or identical structure, which could be advantageous for manufacturing, inventory, assembly, and/or performance.

In some embodiments, methods, materials, and/or means for holding pairs of securement and end plates together other than, or in addition to, ultrasonic welding can be used. In some cases, snap fasteners, screws, rivets, slide fasteners, clips, adhesives, heat staking, solvent welding, or any other suitable attachment technology could be employed.

Figure 12:
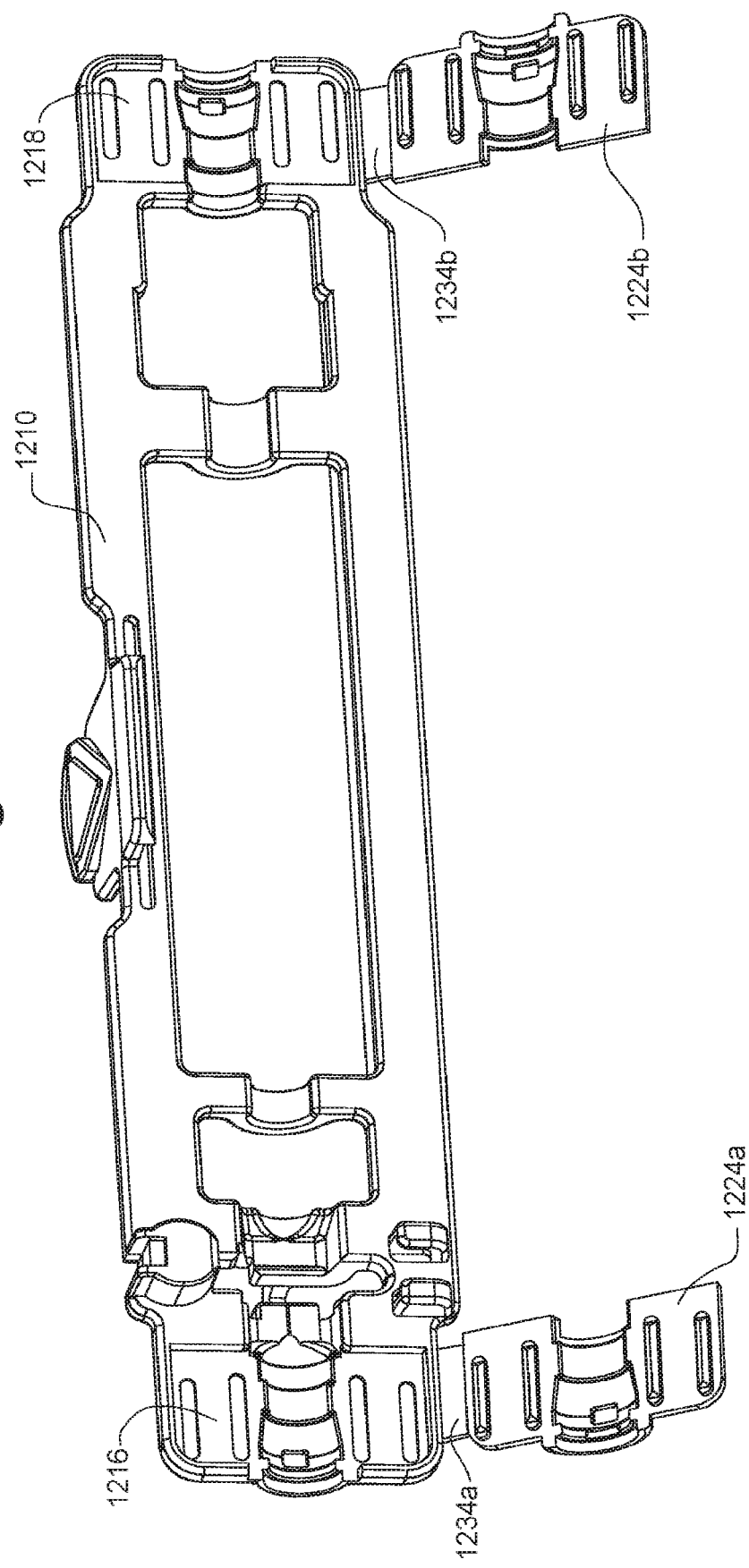
FIG. 12 is a schematic perspective view of an alternative embodiment of a frame for an assembly similar to that of FIGS. 2-7.

In illustrated example assembly 200, securement plates 224a, 224b can be structurally unattached to end plates 216, 218 (as in FIGS. 4 and 5) before the pairs of plates are mated, but other configurations are possible. FIG. 12 is a schematic perspective view of an alternative embodiment of a frame 1210 with end plates 1216, 1218 that are hingedly attached to corresponding securement plates 1224a, 1224b via hinges 1234a, 1234b. Hinges 1234a, 1234b could be thin, flexible elements; frame 1210, securement plates 1224a, 1224b, and the hinges could be manufactured together as a single piece in an injection molding process. This is just one example of how a frame and hingedly attached but un-mated securement plates could be provided. Such an arrangement could be advantageous for manufacturing, inventory, assembly, and/or performance.

With reference again to FIG. 2, et seq., when assembly 200 is assembled (with peristaltic tube 202 coupled to tube couplers 204a, 204b and the tube couplers positioned between mated pairs of end plates 216, 218 and securement plates 224a, 224b), peristaltic tube 202 can be compressed at each end between each end's tube coupler and plates. Compression of peristaltic tube 202 between tube couplers 204a, 204b, end plates 216, 218, and securement plates 224a, 224b can enhance fluidic sealing between the tube and the tube couplers. Dimensions of these components can be selected to affect such sealing, while avoiding problems such as over-compression that could damage materials, and/or cause difficulties in ultrasonic welding.

End plates 216, 218 of frame 210, securement plates 224a, 224b, and tube couplers 204a, 204b can include further features that can cooperate to define or substantially constrain their positional relationship when assembled. End plates 216, 218 and securement plates 224a, 224b can define arcs or ridges 236 that extend into channels 220a, 220b, 226a, 226b. Tube couplers 204a, 204b can define circumferential slots 238 corresponding to ridges 236 such that when securement plates 224a, 224b are mated to end plates 216, 218 with tube couplers 204a, 204b positioned or held therebetween, mechanical correspondence of ridges 236 to slots 238 can substantially constrain tube couplers 204a, 204b translationally with respect to end plates 216, 218 and securement plates 224a, 224b, and also can substantially constrain rotational motion. If rotation about a longitudinal axis aligned with peristaltic tube 202 is defined as "roll," then "pitch" and "yaw" rotations about orthogonal axes can be constrained substantially by mechanical correspondence of ridges 236 to slots 238. "Roll" type rotations of tube couplers 204a, 204b relative to end plates 216, 218 and securement plates 224a, 224b can be substantially constrained by ultrasonic welding, although this is not limiting and other means can be used to constrain roll, such as by way of mechanical keying or adhesive bonding. Energy directors 240 can be provided on securement plates 224a, 224b to facilitate ultrasonic welding of end plates 216, 218 to tube couplers 204a, 204b. Tube couplers 204a, 204b can be rotationally symmetric substantially, about a longitudinal axis. Such substantial symmetry can simplify assembly (discussed elsewhere herein) of assembly 200.

Tube coupler 204a, first end plate 216, and first securement plate 224a can be considered collectively as a first tube support, and tube coupler 204b, second end plate 218, and second securement plate 224b can be considered collectively as a second tube support, where such tube supports are configured to substantially maintain a position of peristaltic tube 202 with respect to frame 210, and with respect to assembly 200. In other embodiments, other hardware configurations could be employed to provide tube supports configured to substantially maintain the position of a peristaltic tube with respect to a frame and assembly. As just one example, although not illustrated, arrangements where tube couplers secure to end plates or the like without securement plates can be contemplated.

Components of assembly 200 can be structured and dimensioned such that, when assembly 200 is assembled, manufactured, or otherwise produced, peristaltic tube 202 is maintained in position with respect to frame 210 such that it is held essentially straight between tube couplers 204a and 204b (or, alternately described, between the first and second tube supports). This can help ensure that tube 202 is properly positioned and aligned with respect to pump 800 and components of pump 800 that interact with tube 202 when assembly 200 is mated thereto or installed therein, as described in further detail elsewhere herein. The length of peristaltic tube 202 can be specified with tolerances to achieve this essentially straight positioning. The length of tube 202 at maximum tolerance can be such that there will be essentially no slack or buckling in the tube when assembled into assembly 200. At shorter lengths than maximum tolerance, such as a minimum tolerance, peristaltic tube 202 can be assembled into assembly 200 with a small amount of tension, slightly stretched between tube couplers 204a and 204b (between the first and second tube supports).

With reference to FIG. 2, et seq., assembly 200 can include features to selectively prevent free-flow of infusate through the peristaltic tube 202. Assembly 200 can include a free-flow prevention (FFP) arm 246 that can be coupled to frame 210 at an arm end 248, and that can include a latching structure 250. Arm 246 can be hingedly coupled to frame 210 via one or more hinge pins 252 (two are illustrated in, e.g., FIG. 4) at arm end 248, and a hinge receiver 254 of frame 210 as illustrated in, e.g., FIG. 5, with hinge receiver 254 having one or more sockets corresponding to the one or more hinge pins 252. In illustrated example assembly 200, hinge receiver 254 is part of or proximate to first end plate 216, but this is not limiting and other locations on frame 210 for FFP arm 246 are possible in some embodiments. The hinge mechanism for FFP arm 246 that includes hinge pin(s) 252 and hinge receiver 254 can be provided such that it does not impart torque and/or rotational bias does not substantially occur between FFP arm 246 and frame 210. In other embodiments, other designs for substantially torque-free hinge mechanisms are contemplated and could be used to couple a FFP arm to a frame.

FFP arm 246 can be manufactured or formed from, or otherwise include, any suitable material or materials. In some embodiments, FFP arm 246 can be formed from acrylonitrile butadiene styrene (ABS). In other embodiments, polycarbonate, polyester, polypropylene, polyvinyl chloride or any other suitable semi-rigid material can be used.

Figure 6:
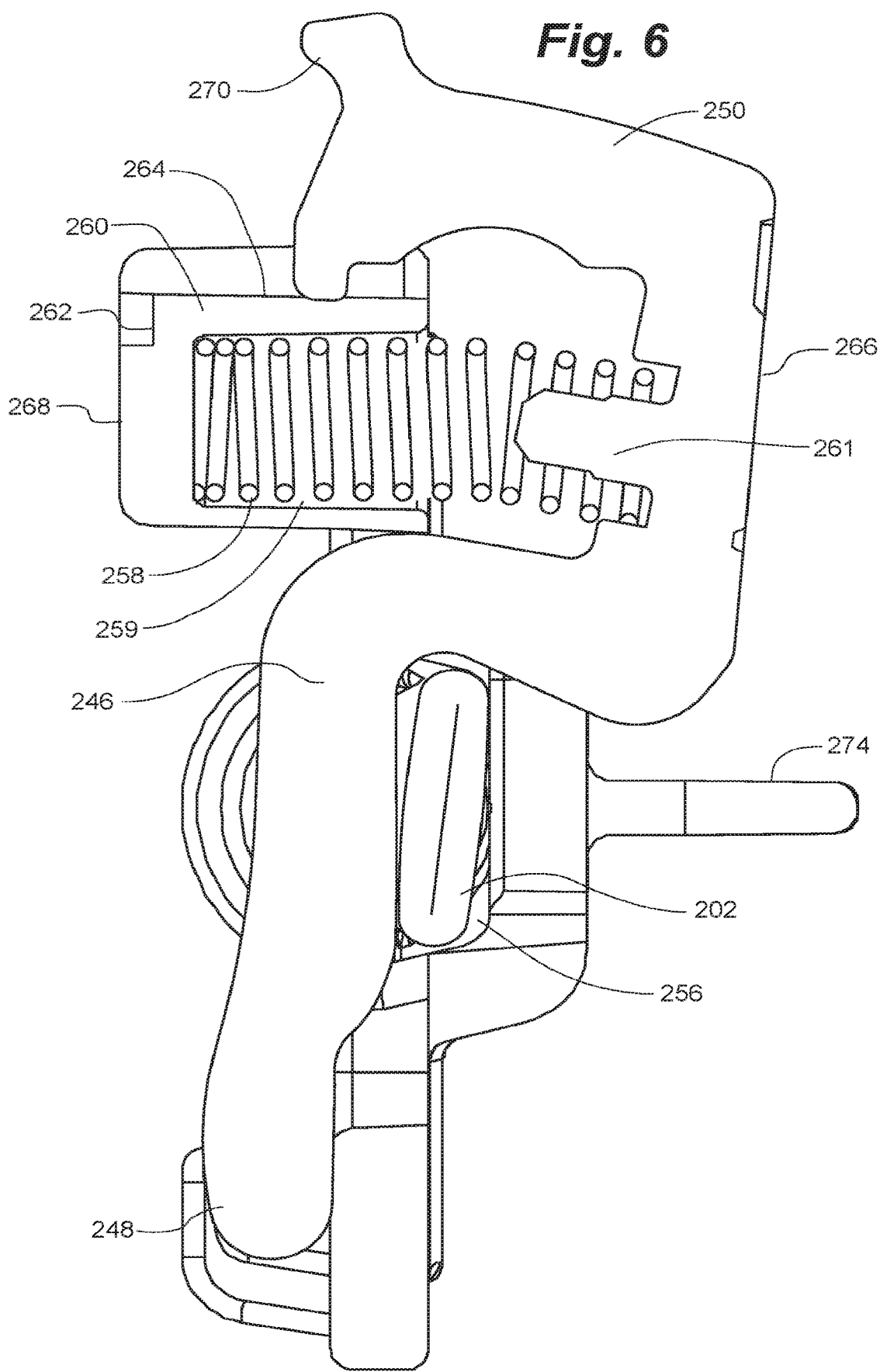
FIG. 6 is a schematic quasi-sectional view of a portion of the assembly of FIG. 2 showing a free-flow prevention arm in a free-flow preventing state.
Figure 7:
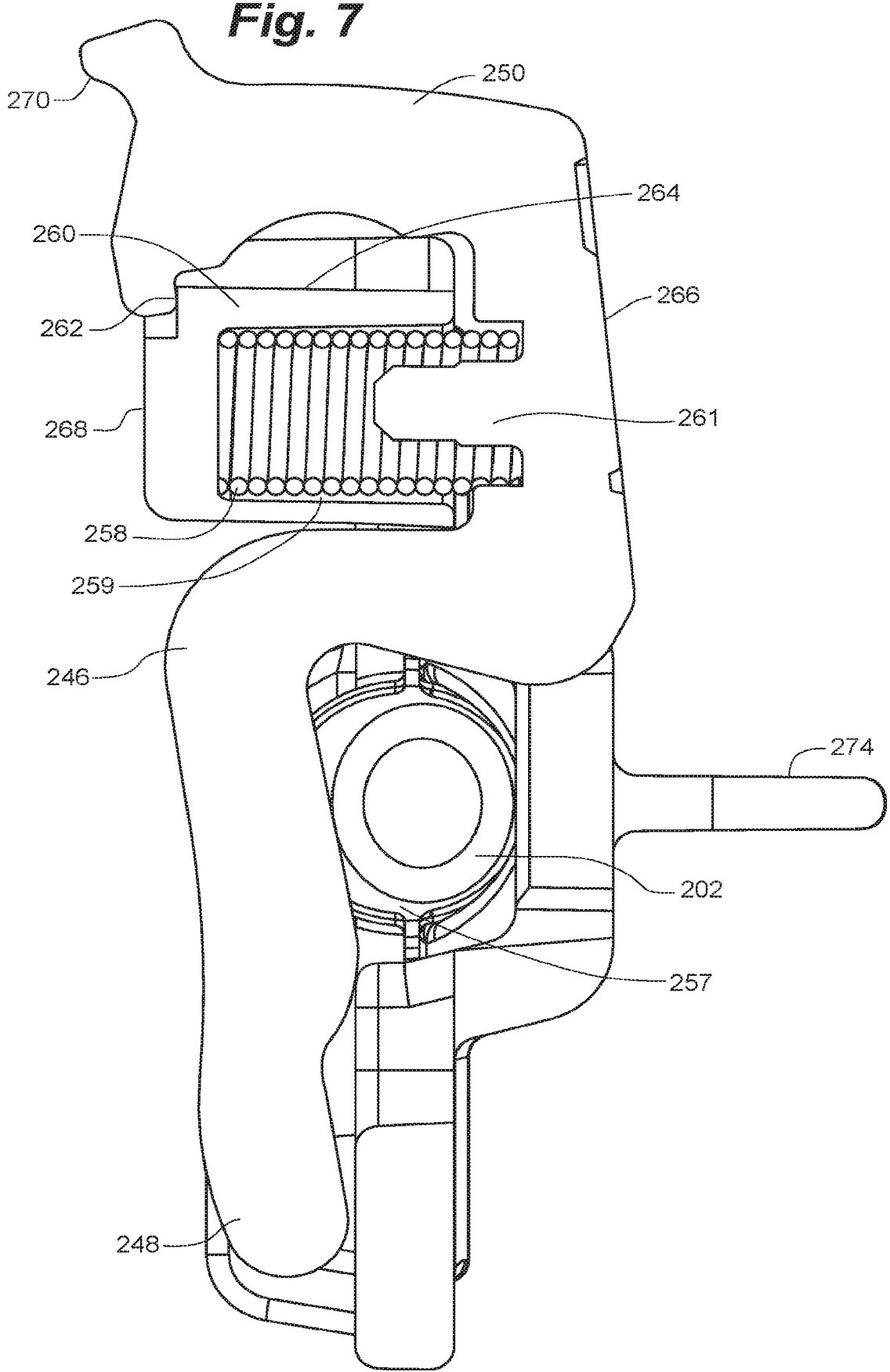
FIG. 7 is a schematic quasi-sectional view of the portion of the assembly illustrated in FIG. 6, showing the free-flow prevention arm in a free-flow allowing state.

FFP arm 246 can be selectively movable relative to frame 210 between a free-flow preventing position and a free-flow allowing position. Examples of these positions are depicted in FIGS. 6 and 7, respectively, which are schematic quasi-sectional views of portions of assembly 200 at a sectional cut through the assembly at the FFP arm 246, as indicated by line A-A in FIG. 2. (The views are not true cross-sectional views, as portions of the assembly further away than the sectional cut are visibly rendered in the views.) In FIG. 6, FFP arm 246 is illustrated in the free-flow preventing position, in which arm 246 and frame 210 can cooperate to squeezingly occlude peristaltic tube 202 in a relatively narrower space 256 between arm 246 and frame 210. (In FIGS. 2 and 3, FFP arm 246 also is illustrated in the free-flow preventing position.) In FIG. 7, FFP arm 246 is illustrated in the free-flow allowing position, in which arm 246 and frame 210 can be relatively positioned to allow peristaltic tube 202 to pass therebetween in a relatively wider space 257 (compared to space 256) between arm 246 and frame 210 such that tube 202 is not squeezingly occluded.

With continued reference to FIGS. 6 and 7, assembly 200 can include a biasing mechanism configured to bias FFP arm 246 to the free-flow preventing position. Assembly 200 can include, for example, a spring 258 that can exert forces on frame 210 and FFP arm 246 to bias arm 246 to the free-flow preventing position. Spring 258 can be any suitable spring, such as a metal coil spring. Spring 258 can be formed separately from frame 210 and from FFP arm 246. Spring 258 can be captured between frame 210 and FFP arm 246. Frame 210 can receive portions of spring 258 in a spring pocket 259, and FFP arm 246 can substantially retain spring 258 at a spring pin 261 as illustrated.

Other configurations of biasing mechanisms are possible. In another embodiment, a biasing force can be provided by a resilient element (such as, but not limited to, a leaf-spring) formed integrally with the frame, but separately from the FFP arm, or formed integrally with the FFP arm, but not the frame. In another embodiment, a biasing force can be provided by a suitable arrangement of magnets.

In another embodiment, although not illustrated herein, an FFP arm can be coupled to a frame via a non-rotating or rigid connection rather than the pin(s) 252 and socketed hinge receiver 254 arrangement as in illustrated assembly 200, with a "hinge" provided by flexure of the FFP arm allowing elastic deformation of the arm between free-flow preventing and allowing positions, and such flexure also providing a biasing force toward the free-flow preventing position.

As depicted in, e.g., FIG. 5, frame 210 can define a slot 272 transverse to the longitudinal axis of peristaltic tube 202 and generally aligned with FFP arm 246. When FFP arm 246 is in the free-flow preventing position, arm 246 can press the peristaltic tube 202 at least partially into slot 272. When tube 202 is squeezingly occluded between FFP arm 246 and frame 210, it may more specifically be squeezed between the arm 246 and one or both edges of frame 210 that define slot 272. Slot 272 can be dimensioned to permit FFP arm 246 to move freely (that is, not to interfere with arm 246) about a typical range of motion of arm 246.

As depicted in, e.g., FIG. 4, frame 210 can include a buttress 274 spanning slot 272. Buttress 274 can be aligned generally with the longitudinal axis of peristaltic tube 202. Buttress 274 can reinforce or stiffen a portion of frame 210 about slot 272 and provide other functions described elsewhere herein. Buttress 274 can be located on a side of frame 210 opposite a side from which FFP arm 246 can press peristaltic tube 202 toward frame 210 and slot 272. Buttress 274 can be located on a same side of frame 210 as a thumb press surface 266 of FFP arm 246 (as shown in, e.g., FIG. 2 and also described further elsewhere herein). Buttress 274 can be located on a same side of frame 210 as a snap release handle 278 (as shown in, e.g., FIG. 2 and also described further elsewhere herein).

With continued reference to FIGS. 6 and 7, frame 210 can include a latching receiver 260 configured to cooperate with latching structure 250 of FFP arm 246, such that latching receiver 260 and latching structure 250 together provide a latching mechanism for FFP arm 246. The latching mechanism can be structured such that it is ergonomically manipulable (in some cases, with a single hand) to latch FFP arm 246 in the free-flow allowing position (shown in FIG. 7), and it can be structured such that it is ergonomically manipulable (in some cases, with a single hand) to unlatch FFP arm 246 to the free-flow preventing position (shown in FIG. 6), as described further herein. The latching mechanism can be regarding as having two states, a latched state (FIG. 7) and an unlatched state (FIG. 6). In the latched state, latching structure 250 can bear against a latching surface 262 of latching receiver 260 such that FFP arm 246 is essentially thereby constrained to a position corresponding to relatively wider space 257 as shown in FIG. 7. In the unlatched state, latching structure 250 can be positioned so that it does not bear against latching surface 262, but rather, structure 250 can slidingly bear against a sliding surface 264 of receiver 260. In the unlatched state, a biasing force such as that provided by spring 258, if present, can bias FFP arm 246 toward the free-flow preventing position corresponding to relatively narrower space 256 as shown in FIG. 6. Sliding surface 264 can be structured with a draft angle that, via interaction with latching structure 250, aids (rather than hinders) motion of the FFP arm 246 toward the free-flow preventing position.

With regard to the potentially ergonomic manipulability of the latching mechanism, latching structure 250 of FFP arm 246 can include a thumb press surface 266 and latching receiver 260 can include a finger press surface 268. While referred to as "thumb" press 266 and "finger" press 268, this nomenclature should not be considered limiting, and the presses 266 and 268 can be manipulated with other than a thumb and finger, respectively. It is anticipated, however, that a common use scenario may be for the latching mechanism to be manipulated with a thumb and an index finger of a single hand. As illustrated in FIG. 6 and FIG. 7, the finger press surface 268 of the latching receiver 260 and the thumb press surface 266 of the latching structure 250 are oriented in an oppositely-disposed manner. As shown, the opposing interaction of the latching structure 250 and the latching receiver 260 separated by spring 259 provides an arrangement in which the finger press surface 268 and the thumb press surface 266 are operatively coupled with one another in close proximity. By manipulating thumb press surface 266 and finger press surface 268 and manually squeezing or urging surface 268 toward surface 266, the latching mechanism can be urged relatively easily and ergonomically into the latched state. As a measure against unintended or accidental movement of the latching mechanism into the latched state, buttress 274 can act as a guard that help prevent an object on the front side of assembly 200 from pressing against thumb press surface 266 or other part of FFP arm 246, thereby providing a guard against accidental latching of the latching mechanism.

The latching mechanism also can be relatively easily and ergonomically manipulated to release the mechanism from the latched state or to unlatch FFP arm 246 such that it can be moved (by, for example, a biasing force of spring 258) to the free-flow preventing position. To aid such a release manipulation, latching structure 250 of FFP arm 246 can include a release catch 270 that a fingertip (for example) can exert force against to release (or, colloquially, "unhook") latching structure 250 from latching surface 262. Release catch 270 can be structured to provide purchase or a suitable surface thereon for a human finger to flex FFP arm 246 sufficiently to unlatch the latching mechanism. Release catch 270 can include one or more side extensions that extend to one or both sides of FFP arm 246 (i.e., perpendicular to a plane of motion of arm 246 relative to frame 200), somewhat resembling a cross-bar of the letter "T" in the illustrated embodiment.

In a non-limiting example of an ergonomic manipulation that can release the latching mechanism from the latched state (shown in FIG. 7), a user can place a thumb on the thumb press surface 266 and/or the buttress 274, and place a fingertip (for example, the tip of the index finger of the same hand as that of the thumb) on release catch 270. With reference to both FIGS. 7 and 6, while bracing or holding the thumb against thumb press surface 266 and/or buttress 274, the user can exert a force generally toward the thumb (that is, to the right of FIG. 6). Under such manipulation, some flexure in FFP arm 246 can allow latching structure 250 to move (upward, toward the top of FIG. 6) such that it no longer bears against latching surface 262. With this constraint removed or minimized FFP arm 246 can move, for example under the influence of the biasing force of spring 258, to the free-flow preventing position of FIG. 6 with peristaltic tube 202 thus being squeezingly occluded. When performing the described manipulation with the index finger and thumb of the same hand, additional fingers of the same or another hand can be used to further brace or support assembly 200 during such manipulations thereof. It has been observed that in some embodiments, the latching mechanism of assembly 200 can be released readily by a user single-handedly, without the use of another hand. As described further elsewhere herein, the latching mechanism of assembly 200 also can be released readily upon coupling of the assembly 200 with an infusion pump.

Figure 8:
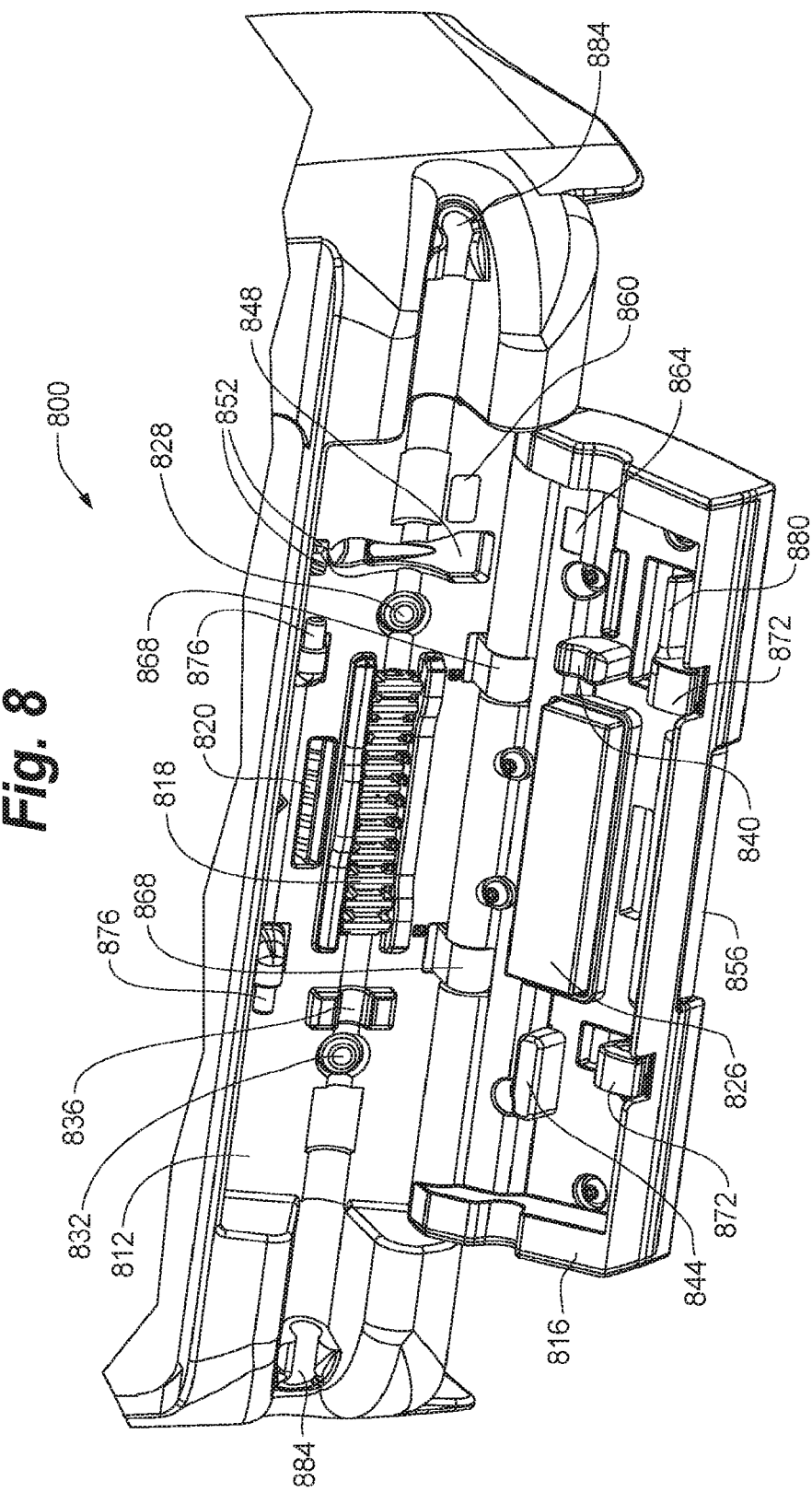
FIG. 8 is a schematic perspective view of portions of an example peristaltic infusion pump, which can be the pump of FIG. 1, particularly illustrating details of an assembly receptacle and a receptacle door of the pump.
Figure 9:
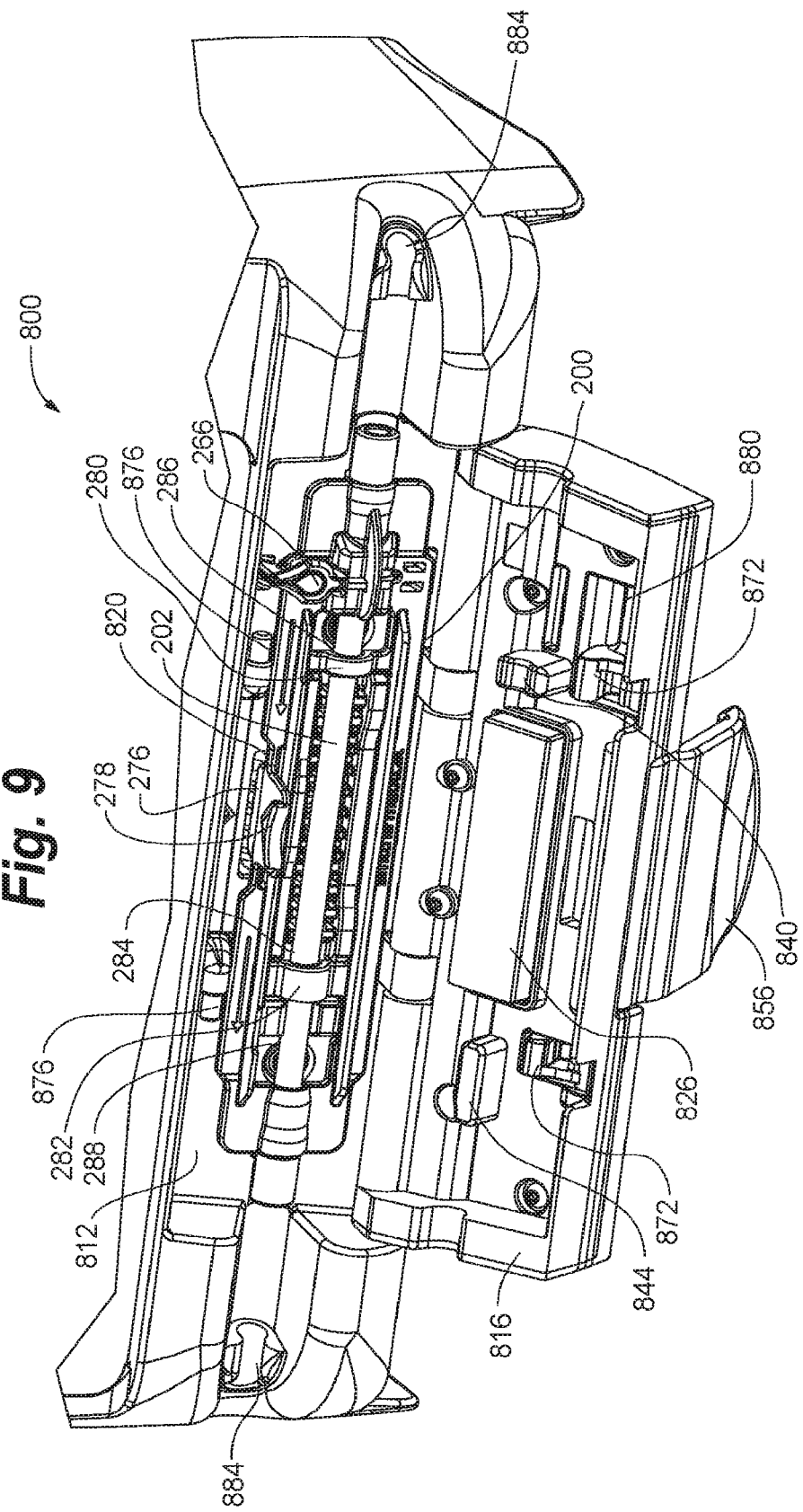
FIG. 9 is a schematic perspective view of portions of the peristaltic infusion pump of FIG. 8, with the assembly of FIG. 2 received by the assembly receptacle of the pump.

FIG. 8 is a schematic perspective view of portions of a peristaltic infusion pump 800, which can be pump 102 of peristaltic infusion pump system 100, particularly illustrating details of an assembly receptacle 812 and a receptacle door 816 of the pump (in an embodiment, corresponding to assembly receptacle 112 and receptacle door 116 of FIG. 1, respectively). Assembly receptacle 812 can be configured to receive assembly 200 of administration set 104 such that the set 104 is thereby operatively coupled to pump 800. FIG. 9 is a schematic perspective view of portions of peristaltic infusion pump 800 of FIG. 8, with assembly 200 received by or installed in assembly receptacle 812. In FIGS. 8 and 9, receptacle door 816 of pump 800 is in an open position.

Frame 210 of assembly 200 can include a snap-fit tab 276 (see FIGS. 2, 3, 4, 5) configured to securely and releasably attach to snap-fit opening 820 of assembly receptacle 812 (as shown in FIG. 8), such that assembly 200 is thereby releasably secured to assembly receptacle 812, and accordingly, administration set 104 can thereby be operatively coupled to pump 800. Snap-fit tab 276 can be formed integrally or otherwise provided with first beam 212 of frame 210, and project away from the first plane of first beam 212 and second beam 214 in a first direction that can be substantially or approximately perpendicular to the first plane. A snap release handle 278 (again, see FIGS. 2, 3, 4, 5) can be formed integrally or otherwise provided with first beam 212, with release handle 278 operatively coupled to tab 276. Release handle 278 can project away from the first plane in a second direction generally opposing the first direction, but other configurations are possible. First beam 212 can incorporate features to provide flexibility for tab 276 and handle 278 relative to other portions of beam 212, such as narrowing of the beam and/or structuring the beam as multiple sub-beams, as illustrated.

Snap release handle 278 and snap-fit tab 276 can be structured such that a defined manipulation of handle 278 can move tab 276 relative to snap-fit opening 820 of assembly receptacle 812 such that tab 276 is releasable from opening 820, and hence assembly 200 is thereby releasable from assembly receptacle 812. The defined manipulation can be, for example, to press or otherwise move snap release handle 278 in a downward direction relative to snap-fit opening 820 of assembly receptacle 812, which can result in snap-fit tab 276 moving upwardly relative to opening 820 of receptacle 812, as handle 278 and tab 276 together flexibly rotate relative to first beam 212. Movement of snap-fit tab 276 upwardly relative to snap-fit opening 820 of assembly receptacle 812 can be such that tab 276 is thereby released from opening 820. In addition, snap-fit tab 276 can be configured such that release from snap-fit opening 820 does not necessarily require that the snap release handle 278 be manipulated. For example, in some instances release of assembly 200 from assembly receptacle 812 can be achieved by pulling tubing (such as upstream tubing 126 and/or downstream tubing 130) away from pump 800. The structural configuration of snap-fit tab 276 may allow it to release from snap-fit opening 820 under the forces existing in such a scenario.

The aforedescribed arrangement for releasably securing assembly 200 to assembly receptacle 812 via snap-fit tab 276 and snap-fit opening 820, and thereby reversibly operatively coupling administration set 104 to pump 800, can be a significant improvement in ergonomics and user-friendliness as compared with other known schemes for coupling administration sets to infusion pumps. In an example manipulation, a user can easily grasp assembly 200 with two fingers (e.g., thumb and index finger) of a single hand via snap release handle 278, move assembly 200 to assembly receptacle 812 of pump 800, and secure assembly 200 to receptacle 812 by pressing snap-fit tab 276 of assembly 200 into snap-fit opening 820 of pump 800. With this arrangement, the user may need only align snap-fit tab 276 with snap-fit opening 820 in order to achieve alignments of features of assembly 200 with corresponding features of assembly receptacle 812 necessary or desirable for operation of infusion pump system 100 (such alignments are described further elsewhere herein). To remove assembly 200 from assembly receptacle 812, a user can ergonomically press down on snap release handle 278, which can move snap-fit tab 276 upwardly and thus out of engagement with snap-fit opening 820, and then with two fingers, ergonomically pull assembly 200 away from receptacle 812.

Assembly 200 and assembly receptacle 812 can include features to prevent adverse outcomes that potentially could result from attempts to improperly insert, couple, or attach assembly 200 to receptacle 812 (and thus correspondingly, e.g., administration set 104 to pump 102). For example, if a user attempts to improperly insert snap release handle 278 into snap-fit opening 820 (with assembly 200 reversed front-to-back, i.e., "backwards" relative to pump 800), physical dimensions of handle 278 and opening 820 can be designed to interfere and prevent such an improper insertion attempt. Also, a potential error to be prevented is unintended depression of thumb press surface 266 or any other part of FFP arm 246 that might result in unintended free-flow of an infusate through tube 202. Assembly 200 and assembly receptacle 812 can be structured such that, when a backwards placement of assembly 200 into receptacle 812 is attempted, other elements of assembly 200 and/or receptacle 812 can interfere before such an improper condition occurs. As noted elsewhere herein, buttress 274 can guard against unintended contact with FFP arm 246. Assembly 200 can include visual cues for the user to encourage proper orientation of assembly 200 when coupling to assembly receptacle 812. This can include text and/or logo(s) (e.g., "smiths medical" on second beam 214, directional arrows on first beam 212, and the tear-drop shape on thumb press surface 266, as illustrated in, e.g., FIGS. 2-5). In some embodiments (not illustrated), an assembly receptacle such as receptacle 812 of pump 800 can include visual cues corresponding to visual cues of assembly 200, such as the aforementioned directional arrows and "smiths medical" logo.

When assembly 200 is secured to assembly receptacle 812 via snap-fit tab 276 of assembly 200 and snap-fit opening 820 of receptacle 812 in pump 800, peristaltic tube 202 of assembly 200 can be positioned for engagement with tube-engaging members 818 of a linear peristaltic pump drive of pump 800. Tube-engaging members 818 (twelve members in the illustrated example of FIGS. 8 and 9, but this is not limiting) can be driven in a coordinated manner by elements of a linear peristaltic pump drive (not illustrated) of pump 800 to thereby urge, push, or transport infusate through, squeezingly, peristaltic tube 202 and thus responsively through other tubes or lines connected fluidically thereto such as (but not limited to) upstream tubing 126 and downstream tubing 130 of infusion system 100 illustrated in FIG. 1.

As illustrated in, e.g., FIG. 2, frame 210 of assembly 200 can include further structures to assist in maintaining a desired position of peristaltic tube 202, such as an upstream cross-support 280 and a downstream cross-support 282 that can span from first beam 212 to second beam 214. Each cross-support 280, 282 can include a curved section to cradle or otherwise supportingly hold peristatic tube 202. When assembly 200 is secured to assembly receptacle 812 in pump 800, cross-supports 280, 282 can also assist in maintaining a proper positon of peristatic tube 202 relative to tube-engaging members 818 of pump 800 such that members 818 are able to effectively engage tube 202.

First beam 212, second beam 214, upstream cross-support 280, and downstream cross-support 282 can define, surround, or bound a pump tube opening or "window" 284 of frame 210. Pump tube window 284 can be substantially free of any structure of assembly 200 other than a portion of peristaltic tube 202 therewithin and generally can correspond to an area where tube-engaging members 818 of pump 800 can engage tube 202 when assembly 200 is secured to assembly receptacle 812 of pump 800. As illustrated in FIG. 8, receptacle door 816 of pump 800 can include a pressure plate 826 that can be, when door 816 is closed and secured (as described in further detail elsewhere herein), positioned along tube 202 generally opposite tube-engaging members 818 such that tube 202 is located between pressure plate 826 and tube-engaging members 818. When in such a configuration, pump 800 and assembly 200 can be structured such that, in an example embodiment, tube-engaging members 818 and pressure plate 826 substantially do not contact frame 210.

As illustrated in, e.g., FIG. 2, portions of frame 210 can define, surround, or bound further windows or openings that can correspond to other areas where components of pump 800 can engage with peristaltic tube 202. For example, first beam 212, second beam 214, upstream cross-support 280, and first end plate 216 can define, surround, or bound an upstream sensor opening or "window" 286 of frame 210; and first beam 212, second beam 214, downstream cross-support 282, and second end plate 218 can define, surround, or bound a downstream sensor opening or "window" 288 of frame 210. Pump 800 can include any or all of, in receptacle 812, an upstream occlusion sensor 828, a downstream occlusion sensor 832, and an air-in-line detector 836, although this is not limiting and other locations, combinations, or arrangements of sensors can be included with pump 800. Upstream sensor window 286 can be substantially free of any structure of assembly 200 other than a portion of peristaltic tube 202 and generally can correspond to an area where upstream occlusion sensor 828 can engage tube 202 when assembly 200 is secured to assembly receptacle 812 of pump 800. Downstream sensor window 288 can be substantially free of any structure of assembly 200 other than a portion of peristaltic tube 202 and generally can correspond to an area where downstream occlusion sensor 832 and/or air-in-line detector 836 can engage tube 202 when assembly 200 is secured to assembly receptacle 812 of pump 800.

Receptacle door 816 of pump 800 can include tube supports 840, 844 that can be, when door 816 is closed and secured about assembly 200, positioned along tube 202 generally opposite, respectively, upstream occlusion sensor 828, and downstream occlusion sensor 832 and air-in-line detector 836, such that tube 202 is located between tube supports 840, 844 and occlusion sensors 828, 832, and air-in-line detector 836. When in such a configuration, pump 800 and assembly 200 can be structured such that, in an example embodiment, sensors 828, 832, detector 836, and tube supports 840, 844, substantially do not contact frame 210. In other embodiments, an assembly similar to assembly 200 can include tubing supports that can provide preload between a peristaltic tube and pump sensors/detectors. Such tubing supports could be included with a frame similar to frame 210 of assembly 200.

As illustrated in, e.g., FIG. 8, assembly receptacle 812 of pump 800 can include features to accommodate and interact with FFP arm 246 of assembly 200. In particular, surfaces of assembly receptacle 812 can define, surround, or bound a recess 848 dimensioned to permit generally unhindered motion of the FFP arm 246 between free-flow preventing and a free-flow allowing positions when assembly 200 is installed in pump 800. Toward a top portion of recess 848, surfaces of assembly receptacle 812 can include at least one latch ramp 852. Latch ramp(s) 852 in receptacle 812 of pump 800 and release catch 270 of assembly 200 can be structured to cooperate so that when assembly 200 is placed in and/or secured to assembly receptacle 812, a portion or portions of release catch 270 (such as side extensions thereof) substantially slide along latch ramp(s) 852 as FFP arm 246 of assembly 200 is moved toward the free-flow allowing position. Contact forces thus exerted on release catch 270 of FFP arm 246 by latch ramp(s) 852 during such sliding interactions can flex the arm 246 sufficiently to prevent the latching mechanism from latching in the free-flow allowing position. As discussed elsewhere herein, FFP arm 246 can be moved toward the free-flow allowing position when receptacle door 816 is closed and a door latch lever 856 is moved from its unlatched position (as illustrated in, e.g., FIG. 10) to its latched position (as illustrated in, e.g., FIG. 11). Latch ramp(s) 852 can substantially inhibit or prevent the latching mechanism from latching in the free-flow allowing position during such an action. Furthermore, if the latching mechanism is latched in the free-flow allowing position before assembly 200 is secured to assembly receptacle 812, then when assembly 200 is secured to receptacle 812 (by pressing snap-fit tab 276 into snap-fit opening 820 as aforedescribed), latch ramp(s) 852 can exert force on release catch 270 sufficient to flex FFP arm 246 enough that the latching mechanism is released, thereby allowing FFP arm 246 to be biased (for example, by spring 258) to the free-flow preventing position. This can be an important safety feature, helping to ensure that administration set 104 is in a non-free-flow state initially when it is secured to the pump.

As illustrated in, e.g., FIG. 8, assembly receptacle 812 of pump 800 can include an optical device 860 that can be configured and used to detect a presence of and/or identify a particular or different type or unit of assembly 200 received by assembly receptacle 812 of pump 800. An optical reference/calibration portion 864 can be included in or on door 816, generally within view of optical device 860 when door 816 is closed and assembly 200 is not received by assembly receptacle 812. Optical device 860 can include any suitable hardware for optical detection/identification, including but not limited to light sources, imaging and/or non-imaging light sensors, polarization-active components, and light redirecting components, such as refractive, reflective, and/or diffractive elements. In some embodiments, optical device 860 can be configured to detect color, and particular or different types or units of assembly 200 can be differently or uniquely colored to encode different infusion applications, therapies, or procedures for which their corresponding administration sets 104 are configured and intended. For example, in some healthcare environments, a yellow color scheme is commonly identified by medical practitioners as pertaining to epidural procedures, and an orange color scheme is commonly identified by medical practitioners as pertaining to enteral procedures. (It should be noted that such color associations are not necessarily universal and may vary between hospitals, institutions, regions, practices, etc.) In some embodiments, a substantial portion or essentially all of frame 210 of assembly 200 can bear or exhibit a color identifying a particular infusion application, therapy, or procedure. The use of such identifying colors may permit caregivers to quickly recognize an intended application, therapy, or procedure for an administration set 104, and optical device 860 can provide the controller of pump 800 with administration set identifying information. With such information, the controller could then configure or program itself and/or pump 800 for the infusion application, therapy, or procedure.

Figure 10:
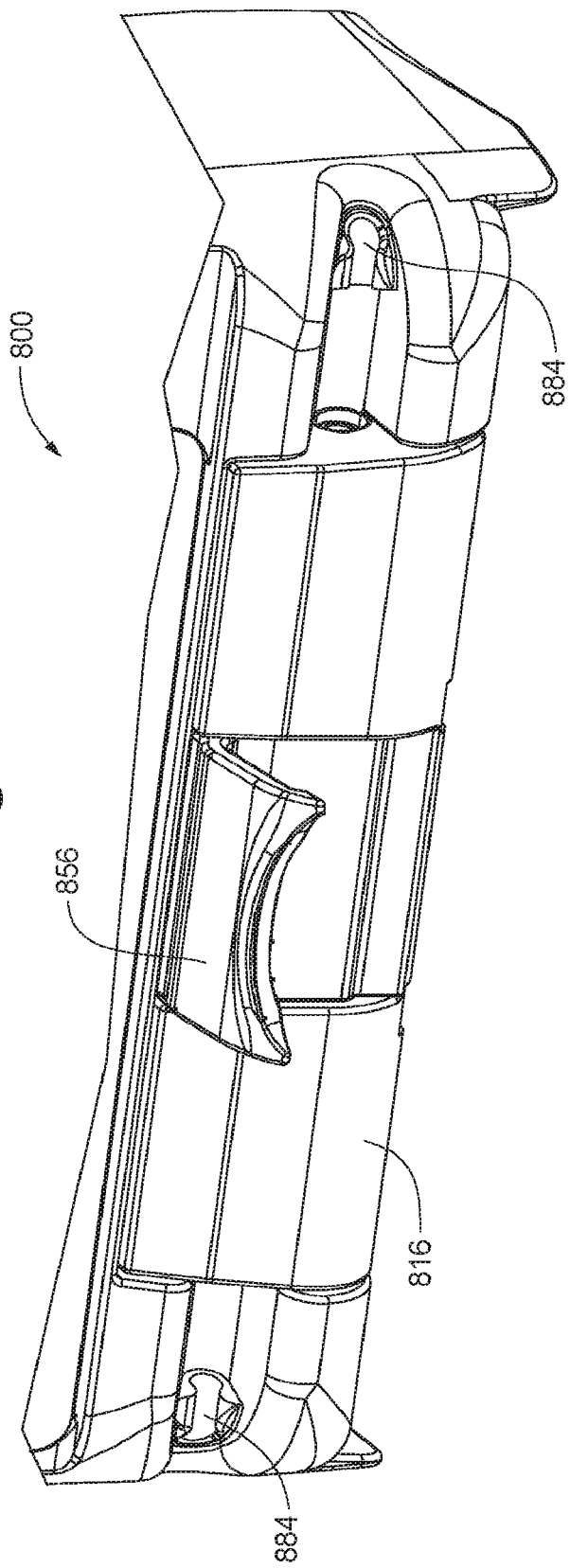
FIG. 10 is a schematic perspective view of portions of the peristaltic infusion pump of FIG. 8 with the receptacle door in a closed position and a door latch lever in an unlatched position.
Figure 11:
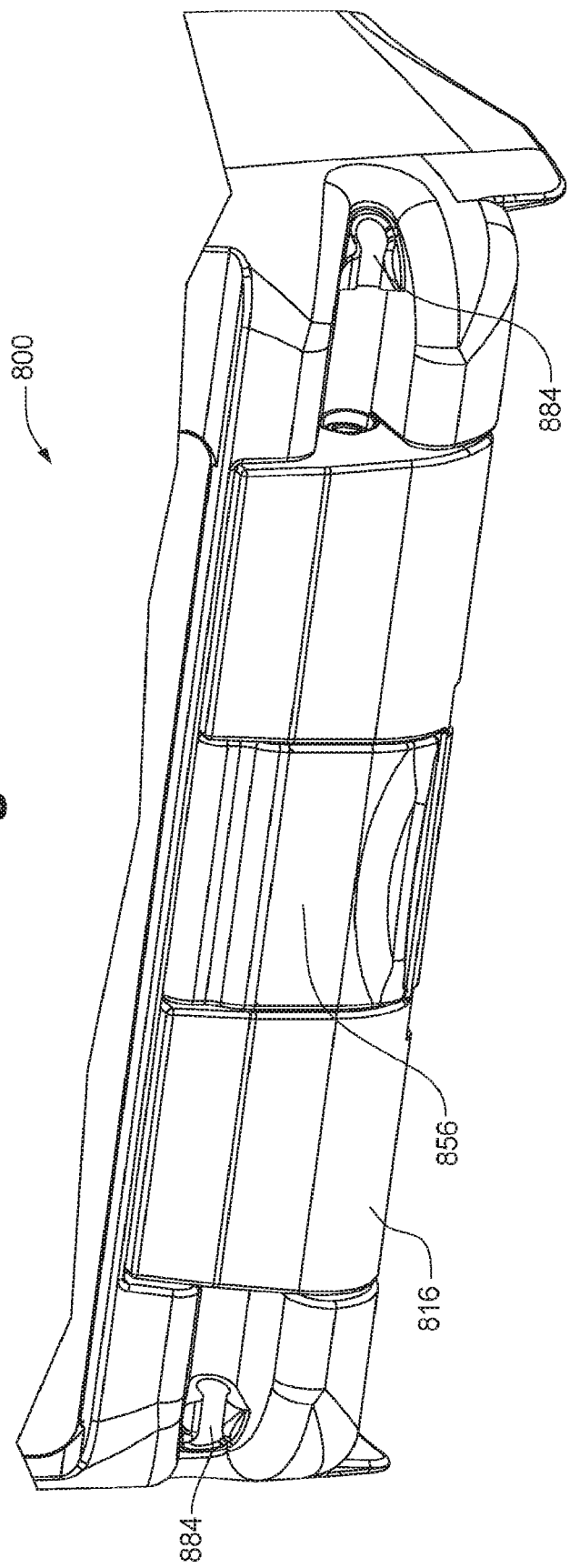
FIG. 11 is a schematic perspective view of portions of the peristaltic infusion pump of FIG. 8 with the receptacle door in the closed position and the door latch lever in a latched position.

After assembly 200 is received by assembly receptacle 812, door 816 can be rotated closed about hinges 868 (as shown in, e.g., FIG. 8) and door latch lever 856 can be moved from an unlatched position to a latched position as shown in FIGS. 9-11. FIG. 10 is a schematic perspective view of portions of pump 800 with door 816 in the closed position and door latch lever 856 in the unlatched position. FIG. 11 is a schematic perspective view of portions of pump 800 with door 816 in the closed position and door latch lever 856 in the latched position. It is to be understood that in FIGS. 8 and 9, door 816 is in a fully or substantially open position, but the door latch lever 856 is arbitrarily in what would otherwise be the latched position in FIG. 8 and the unlatched position in FIG. 9, to illustrate features on an interior of door 816 that depend on position or movement of door latch lever 856. For example, as shown in FIGS. 8 and 9, door 816 can include one or more door latch hooks 872 corresponding to one or more door latch pins 876 of receptacle 812. Door latch hooks 872 can be mechanically linked to door latch lever 856 to responsively move as lever 856 is moved between latched and unlatched positions. When door 816 is closed and door latch lever 856 is in the latched position, door latch hooks 872 can be responsively positioned relative to door latch pins 876 to engagingly constrain or latch door 816 in the closed position. When door latch lever 856 is in the unlatched position, door latch hooks 872 can be responsively positioned to dis-engagingly not interfere with door latch pins 876 as door 816 is moved into and out of the closed position.

As also shown in FIGS. 8 and 9, door 816 can include an FFP arm pusher 880 that can be mechanically linked to door latch lever 856 to move as lever 856 is moved between latched and unlatched positions. In some embodiments, FFP arm pusher 880 can be provided integrally on a structure of door latch hook 872. FFP arm pusher 880 can be operatively coupled to door latch lever 856 and configured such that when assembly 200 is received by assembly receptacle 812 and door 816 is closed, FFP arm pusher 880 pushes FFP arm 246 (for example, by exerting force on arm 246 at thumb press surface 266 and/or other parts of arm 246) from the free-flow preventing position to the free-flow allowing position as door latch lever 856 is moved to the latched position. When door latch lever 856 is returned to the unlatched position, FFP arm pusher 880 can responsively retract, thereby allowing the biasing force provided by, for example, spring 258 to return FFP arm 246 to the free-flow preventing position. As described elsewhere herein, latch ramp(s) 852 can prevent the aforementioned latching mechanism for FFP arm 246 from latching when assembly 200 is received by assembly receptacle 812. The arrangement described herein can be an important safety feature, to aid in substantially ensuring that FFP arm 246 is in the free-flow preventing state when the door 816 is opened and assembly 200 is removed from pump 800.

To review an example of operation of cooperative and/or responsively actuated free-flow protection mechanisms of assembly 200 and pump 800, a potential sequence of actions is presented here with reference to FIGS. 1-11. An administration set 104 that includes assembly 200 can be coupled to an infusate reservoir such as an IV bag 120. Optionally, to prime administration set 104, a caregiver can latch FFP arm 246 of assembly 200 into the free-flow allowing state with the latching mechanism. After priming, the caregiver can unlatch the latching mechanism by, for example, manipulating release catch 270 as aforedescribed. The caregiver can secure assembly 200 to assembly receptacle 812 by grasping snap release handle 278, moving assembly 200 to receptacle 812, and pressing snap-fit tab 276 into snap-fit opening 820. If the latching mechanism remains latched immediately before assembly 200 is placed into or secured to receptacle 812, then as tab 276 is pressed into opening 820, latch ramp(s) 852 can exert force on release catch 270 sufficient to release the latching mechanism, and FFP arm 246 can thereby be biased (for example, by spring 258) to the free-flow preventing position.

With assembly 200 secured to assembly receptacle 812, the caregiver can then close door 816. As door 816 is rotated or moved into its closed position, pressure plate 826 can come into position along a portion of peristaltic tube 202 opposite tube-engaging members 818, and tube supports 840, 844 can come into position along a portion of tube 202 opposite occlusion sensors 828, 832 and detector 836. To bring door 816 to its fully-closed position, if door latch lever 856 is in the latched position, it may be necessary to move it to the unlatched position, otherwise door latch hooks 872 may interfere with latch pins 876. With door 816 in its fully-closed position, door latch lever 856 can be moved to the latched position. As door latch lever 856 is moved to the latched position, door latch hooks 872 can responsively move as aforementioned to their latched positions where they can extend or hook around door latch pins 876 to aid in preventing door 816 from unintentionally opening. As door latch hooks 872 are moved to their latched positions, FFP arm pusher 880 can progressively push FFP arm 246 to the free-flow allowing position. However, with door 816 fully closed, some tube-engaging members 818 and pressure plate 826 can occlude tube 202 simply by virtue of their presence and thus prevent free-flow, even with FFP arm 246 in the free-flow allowing position.

At any suitable time, which may be before or after door 816 is closed, upstream and downstream tubing 126, 130 (not illustrated in FIG. 9-11) can be manually pressed into tube guides 884.

After completion of infusate delivery by pump 800 or at any suitable time, door latch lever 856 can be moved from the latched to the unlatched position before opening door 816. As door latch lever 856 is moved to the unlatched position, FFP arm pusher 880 can retract, allowing FFP arm 246 to be biased to the free-flow preventing position. After door 816 is opened subsequently, assembly 200 can be released from assembly receptacle 812 via manipulation of snap release handle 278, and administration set 104 can be decoupled, disengaged, or removed from pump 800 with FFP arm 246 in the free-flow preventing position. Prior to moving door latch lever 856 to the unlatched position, free-flow would be prevented by tube-engaging members 818 and pressure plate 826 as aforementioned. Thus, prevention of free-flow can be maintained substantially continuously from when assembly 200 is secured to assembly receptacle 812, to a later time after the assembly is removed from the receptacle.

Of note, any or all of the actions in the aforedescribed potential sequence of actions can be performed using only a single hand (for example, but not necessarily limited to: latching and unlatching FFP arm 246, securing and releasing assembly 200 to/from receptacle 812, closing and opening door 816, and moving door latch lever 856 between latched and unlatched positions). This can contribute significantly to ease of use of the infusion pump system.

It is to be appreciated and understood that, although not illustrated in the Figures, in another embodiment an assembly similar in some aspects to assembly 200 can be provided that includes free-flow protection, but no latching mechanism, and/or a different latching mechanism structure or configuration. A free-flow protection arm can be provided that does not include a latching structure like latching structure 250 of FFP arm 246. Without a latching structure, such an alternative free-flow protection arm would not necessarily need to provide flexure (which FFP arm 246 can provide to enable release of latching structure 250 from latching receiver 260 as shown in, e.g., FIGS. 6 and 7). Such a free-flow protection arm could be configured to be, for example, compatible with assembly receptacle 812 of pump 800, and particularly, be operable with FFP arm pusher 880 to move the free-flow protection arm between free-flow allowing and preventing positions as door latch lever 856 is moved between latched and unlatched positions, respectively.

It is also to be appreciated and understood that, although not illustrated in the Figures, in another embodiment that does not have a latching mechanism that is integrally provided with a free-flow protection arm and frame, a separate latching clip or device could be provided to secure the free-flow protection arm in a free-flow allowing position for purposes such as priming or gravity administration. Such a separate latching clip or device could be shaped or structured such that the latching clip or device prevents (for example, via mechanical interference) operatively coupling the assembly to the pump when the clip or device is securing the free-flow protection arm in a free-flow allowing position. Thus, the separate clip or device would be detached or deactivated prior to operatively coupling the assembly to the pump, thereby satisfying free-flow safety objectives or requirements.

Alternatively, or in addition to the arrangement shown in FIG. 8 having an optical sensor 860, other sensing devices or means 860A (as will be described with reference to, e.g., FIG. 13) for identification of an assembly 200 are contemplated as well. Such sensing devices 860A can be used to readily identify an intended "route" of infusion, application, therapy, procedure, or other grouping of assemblies 200.

Figure 13:
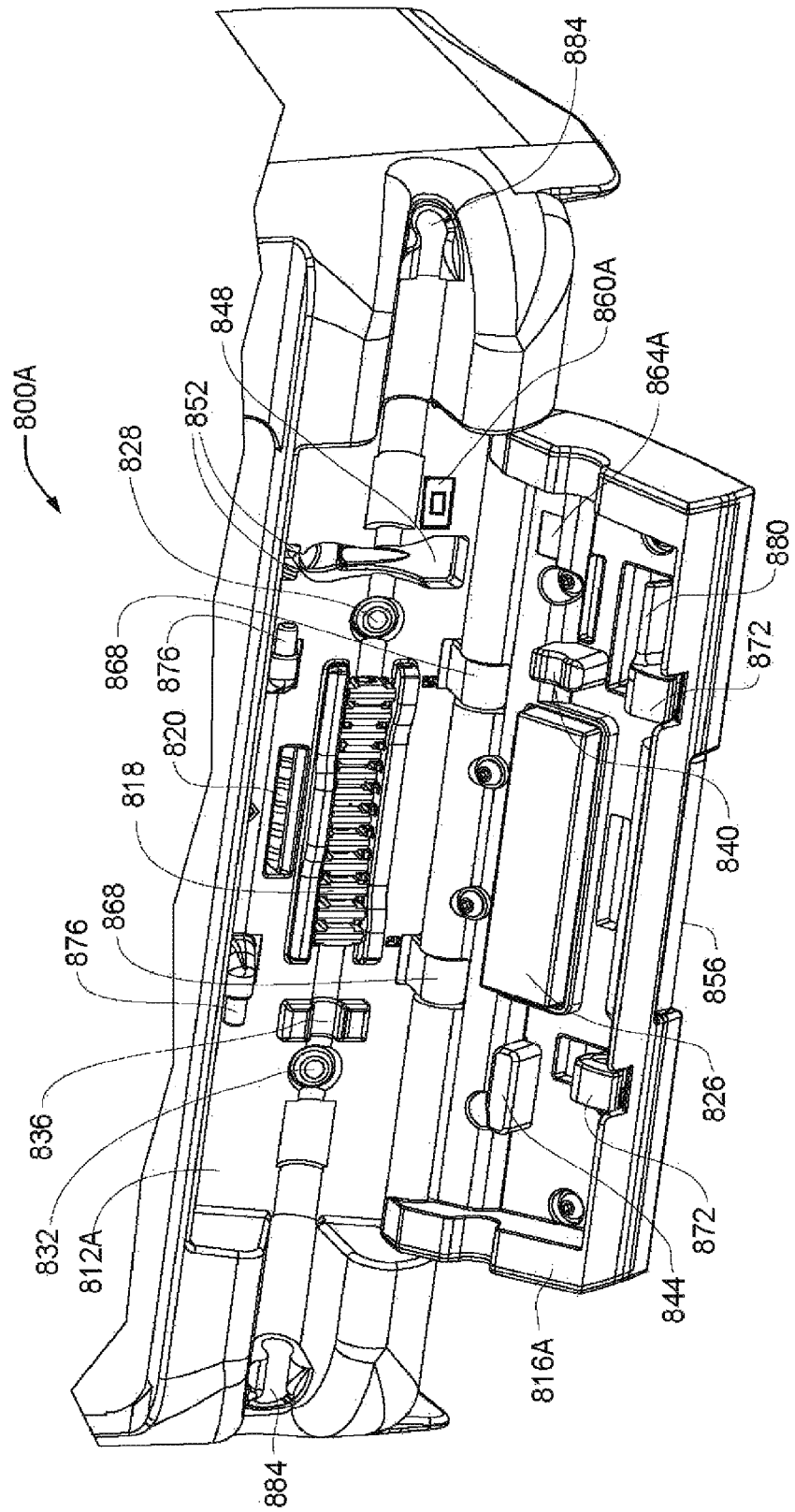
FIG. 13 is an alternative embodiment of a schematic perspective view of portions of an example peristaltic infusion pump, which can be the pump of FIG. 1, particularly illustrating details of an assembly receptacle and a receptacle door of the pump.

Some examples of alternate sensing devices 860A are disclosed and described in FIGS. 13-17C and the following discussion. In FIG. 13, a pump 800A is shown having an assembly receptacle 812A and a sensing device 860A. To the extent features of FIG. 13 are not specifically described in the following disclosure, they should be understood as being consistent with the discussion and corresponding reference numerals associated with FIG. 8. A corresponding assembly 200A for mating with the pump 800A of FIG. 13 is shown in FIG. 14. To the extent features of FIG. 14 are not specifically described in the following disclosure, they should be understood as being consistent with the discussion and corresponding reference numerals associated with FIG. 3.

In general, sensing device 860A of FIG. 13 can be one or more sensors of various types and detection capabilities. In some embodiments, identification sensor 860A can include components for detection based on one or more of: magnetic keying, pin configurations, size, shape, radio frequency identification (RFID), near field communication (NFC), or other identification technology. In certain embodiments, sensing device 860A could include variations of an optical sensor 860, as described earlier in FIG. 8, as well.

Grouping of assemblies 200A based on an assembly's intended "route" (i.e. location where the medication is going) of medication delivery can have a variety of benefits especially when these groups can be rapidly and reliably identified by using sensing devices 860A (or 860). In some embodiments, one or more of the sensing devices 860A allow a pump to detect the intended "route" of infusion based on identifiers present on an attached assembly 200A. For example, the "route" of infusion could include delivery: intravenously, via mouth, via feeding tube; or via alternate injection location. Identification of the "route" can be a useful grouping as the route can define the hardware needed. Accordingly, knowing the "route" is typically determinative of the assembly 200A (or larger disposable set) needed to accomplish a particular infusion. Sensing the route of infusion, not just the physical properties of the assembly being used, provides an assembly type or disposable set tied to the performance of the pump, and allows for automatically filtering the drug library to correspond to that assembly type or disposable set. PCT patent publication WO2016/018552A1 to Blomquist, published Feb. 4, 2016, entitled "Medicament Infusion System and Pump Assembly for Use Therein, further relates to identifying an infusion route to a pump and other systems, methods and material, and is hereby fully incorporated by reference herein.

Detection of identification information of the assembly 200A can be useful both for authentication purposes as well as for ease of programming purposes. With respect to authentication of the assembly 200A, verification that the assembly 200A is being delivered via the correct route, or in accordance with another parameter, will help to reduce user errors and provide a method of identifying authentic assemblies 200A. Identifying authentic assemblies 200A which are made according to approved specifications and/or by authorized suppliers can provide desirable safety benefits to users as well.

With respect to programming, detecting the route of infusion enables the pump 800A to automatically begin the programming process for a desired route or type of administration upon attachment of the disposable assembly 200A to the compatible infusion pump. Immediate recognition of this information by the pump can simplify the programming steps required for infusion to occur, shorten the time-period to begin infusion, and eliminate certain sources of potential programming errors.

FIG. 14 sets forth an example of an assembly 200A, similar to the arrangement of FIG. 3, in which a back schematic perspective view of the assembly 200A can be seen. In FIG. 14, one or more areas on the assembly 200A serve as an identifier 861A, based on color or other identifying feature. In some cases, the identifier 861A is a colored surface or tag. In some embodiments, this color can provide an associated visible or infrared optical wavelength for detection. As depicted on FIG. 14, the flat area on securement plate 224a could be used for an identifier 861A, for example.

Therefore, a general peristaltic pump identification arrangement can be understood from a combination of the components of FIGS. 13 and 14. Specifically, a general identification arrangement may include a sensing device 860A on a pump 800A (as shown in FIG. 13) and an identifier 861A on the assembly 200A (as shown in FIG. 14). Although dependent on the identification technology used, in general, the sensing device 860A serves as a "reader" and the identifier 861A, located on a mating assembly 200A, serves as the source of identification data. Assembly 200A can be constructed with an identifier permanently installed or coupled to the assembly 200A in some embodiments. The mating infusion pump 800A would have an appropriate reader or sensing device 860A to automatically identify the assembly 200A being attached to the infusion pump 800A to begin the programming process. Using this type of identification arrangement provides a robust method of identifying assemblies 200 and reduces user error.

In some embodiments, the identifier 861A may relate to the color of the tubing passing through the assembly 200A, rather than a separate identifier 861A on the assembly 200A. Further, the identifier 861A may be understood to be located on any type or configuration of assembly 200A and is not limited in any way by the assemblies and embodiments disclosed herein in the figures or specification. Certain assemblies may include one or more identifier(s) 861A on a frame 210 defining the assembly. Other embodiments include one or more identifier(s) 861A just outside an assembly frame structure 210. Other embodiments may relate to identifiers 861A on a non-unitary frame and/or multi-part frame structure. Some assemblies may have no specifically-defined frame structure at all.

In some embodiments, identifiers 861A could be sensed on or in as part of component parts of an assembly 200A such as Y-sites, stopcocks, the FFP arm 246, the FFP spring 258, slide clamps or tube couplers. Likewise, the sensing device 860A used may be viewed as non-limiting in various respects. The sensing device 860A may be aligned outboard of the frame 210 or inboard of the frame 210.

Detection of assemblies 200A based on magnetic keying can be utilized for identification in some embodiments. In these embodiments, the sensing device 860A can include a Hall Effect sensor or other device used to vary an inductive field. The sensing device 860A can function as a reader of a magnetic key or identifier 861A on the assembly 200A. Accordingly, the identifier 861A provides identification data via the magnetic key.

In some magnetic key arrangements, sensing devices 860A sense a rotating magnetic field via an encoder. In some embodiments, a microprocessor chip can be mounted to the pump 102. The device can be arranged such that different disposables will provide a different magnetic orientation. In some linear magnetic embodiments of sensing devices 860A, sensors will place North/South magnets (i.e. shown as "N" for North and "S" for South in the figures) in a row. In some embodiments, industrial motor sensors will provide absolute or relative positions. Such sensing arrangements can provide the ability to utilize a single sensor to sense multiple keys.

Figure 15A:
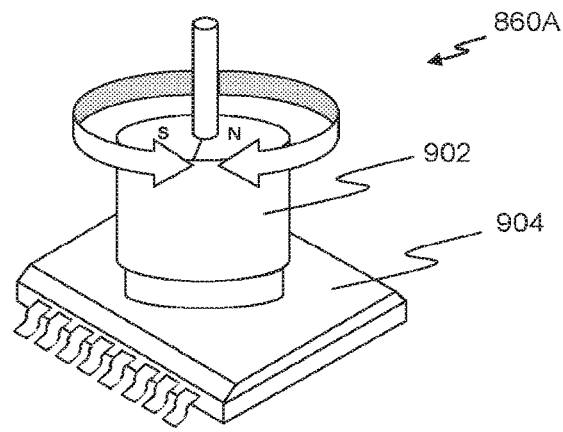
FIGS. 15A-E are examples of sensing devices of a pump utilizing magnetic keying devices for assembly identification or information.

FIGS. 15A-E provide examples of sensing devices 860A capable of providing magnetic keying capabilities. FIG. 15A shows a sensing device 860A comprised of a magnetic rotary encoder 902 on a processing chip 904. Sensors of this type may be contactless and integrate field sensing Hall elements, analog front-end, and digital signal processing in some embodiments. The rotary position is contactlessly sensed by a small rotating magnet that is placed above the device to identify a particular assembly or designated "route". Small absolute positions of a full turn may be sensed in some embodiments permitting resolutions of factions of a degree in some cases.

Figure 15B:
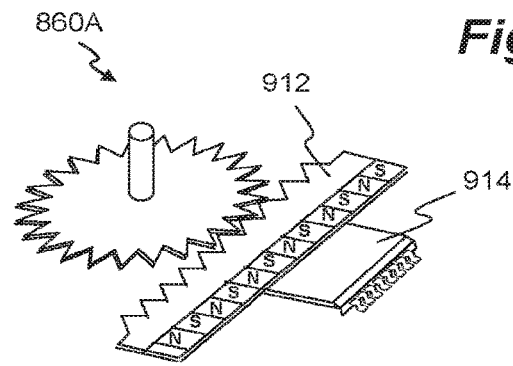
Figure 15C:
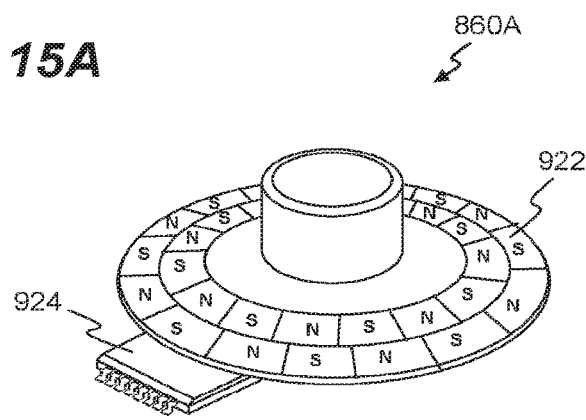

FIGS. 15B and 15C depict sensing devices 860A which can rely on magnetic keying by detecting linear motion and off-axis rotational measurements. FIG. 15B shows an example of a sensing device 860A combining Hall effects and a signal processor. Specifically, magnetic strips 912 having a pole-pair are coupled with signal processor 914. Accordingly, assembly identification/information can be obtained based on linear magnetic movement. In FIG. 15C, another embodiment is shown containing a pole-paired magnetic rings 922 and signal processor 924. Pole-paired magnetic rings 922 like this can provide a very high resolution of positions per revolution and can operate at significant RPMs.

Figure 15D:
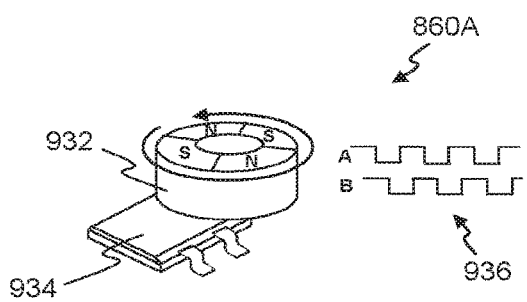
Figure 15E:
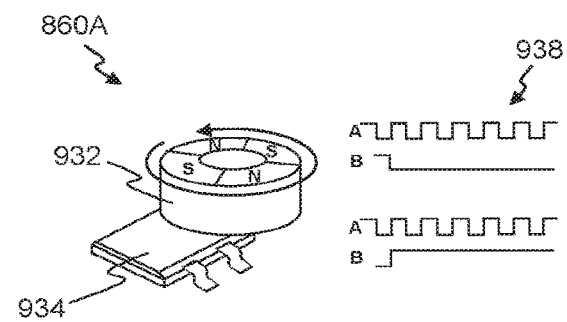

FIGS. 15D and 15E shown examples of sending devices 860A that utilize magnetic keying with sensors including a Hall effect latch which detects both "vertical" and "horizontal" magnetic fields at the same time. These each contain a magnetic rotary encoder 932 and processor 934. As shown in FIG. 15D, the results can be read out to A and B pins as depicted at 936. In FIG. 15E, pulse and rotational direction can be output as depicted at 938. Numerous variations and/or combinations of such magnetic keying devices may be utilized as sensing devices 860A.

In other embodiments, detection of assemblies 200A can be based on keyed pin configurations. These pin configurations can be mechanical or electrical and can include push pins or interfaces for receiving patterned pin arrangements on the sensing device 860A. The particular identifying geometry present on the corresponding assembly 200A will communicate the intended route or other identifying information to the sensing device 860A. Examples of possible sensing device configurations with receptacles or contacts 940 for receiving or providing engaging pins are shown in the top view depictions of FIGS. 16A-C and the perspective view embodiment of FIG. 16D. Corresponding engaging pins or contacts would be present on the identifier 861A of the assembly 200A.

In some embodiments, the pin configuration or patterned arrangement will be presented as an electric matrix array. Accordingly, such sensing devices 860A permit simultaneous force measurements across a grid of cells. Matrix arrays can be used for capturing static and dynamic footprints or multi-touch user inputs in some embodiments. In some cases a matrix arrangement can even include memory to store more detailed information that could be received by a pump 102.

Detection using pins or other features can rely upon physical geometries, as referenced in FIGS. 16A-D. Alternatively, electrical geometries may be utilized. Rather than detection by shapes or mechanical pins relying on an on/off switch, a force sensor array is used to detect an amount of force. Electric geometries can rely upon sensing variable resistance with a sensing device to interpret the electric geometries presented. Accordingly, the "keys" are the means for providing variable resistance associated with a particular assembly. In some cases, capacitance or inductance could be used as "keys" as well. In some cases electrical geometries can even include memory to store more detailed information that could be received by a pump 102.

Figure 16A:
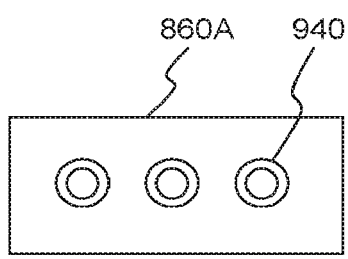
FIGS. 16A-D are top and perspective view examples of sensing devices of a pump for receiving pin configuration identifiers for assembly identification or information.
Figure 16B:
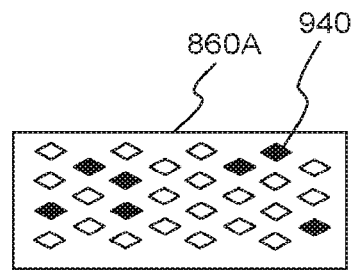
Figure 16C:
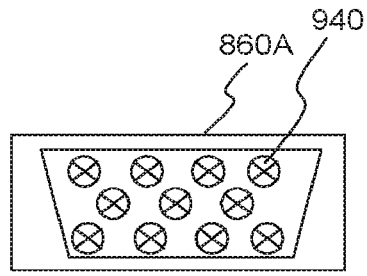
Figure 16D:
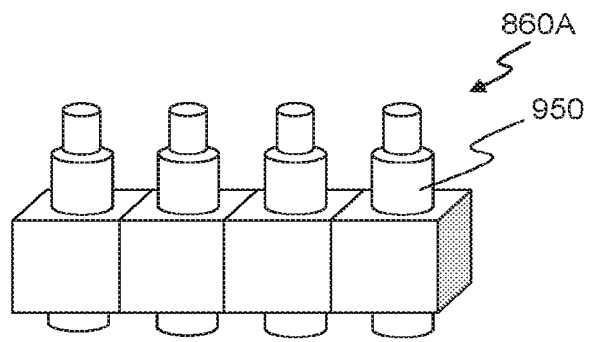

FIG. 16D shows one example of a pogo-pin design which can be based on mechanical and/or electrical geometries. Pins 950 provide "keys" to identifying an attached assembly 200A (or information, such as medication "route") to an assembly receptacle 812A or a pump 102. Some pogo-pins may include internal springs or other resilient mechanisms for making contacts, for example.

Figure 17A:
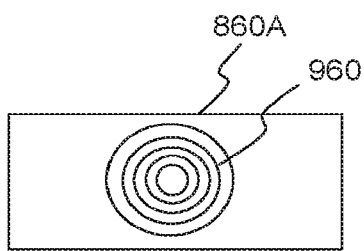
FIGS. 17A-C are top view examples of sensing devices of a pump for receiving protrusions of various shapes and sizes for assembly identification or information.
Figure 17B:
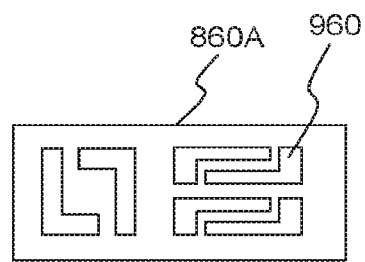
Figure 17C:
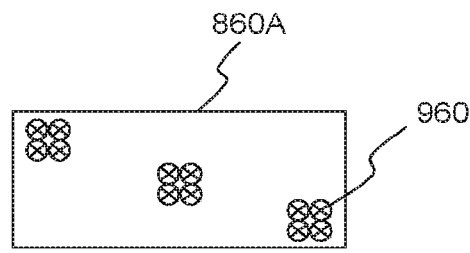

Other forms of identification and detection based on identifying protrusions of particular sizes and shapes are possible as well. In certain embodiments, features are present on the sensing device 860A for matching and detecting geometric features of an assembly 200A. Features present on the sensing device 860A can include flanges or nested recesses 960, for example. Examples of interfaces or design features of possible sensing devices 860A for receiving specially sized and shaped protrusions present on identifier 861A of assemblies 200A are shown in FIGS. 17A-C.

As discussed above, detection using specifically shaped features can rely upon physical geometries or electrical geometries. A force sensor array may be used to detect an amount of force in some instances. Electric geometries can rely upon sensing variable resistance, etc. Sensing resistance, capacitance or inductance can be used as "keys".

Detection of characteristics of an assembly 200A can also be based on RFID technology. In some embodiments, an RFID reader can be used as the sensing device 860A within the pump 800A. Further, the assembly 200A can provide an RFID tag, as an identifier 861A, which could store and provide various pieces of information to the RFID reader regarding the assembly 200A. This information may include one or more of: "route" of infusion, application, therapy, procedure; date of manufacture; lot number of manufacture; manufacturing site; date of expiration; use; primary volume; upstream volume; downstream volume; alarms; programming information; for example. Tracking manufacture information has many uses and can enable additional safety and functionality options. For example, tracking manufacture information can help ensure that any issues that are encountered with assemblies 200A can be readily isolated and dealt with promptly. Tracking information can be used to trigger a variety of alarms. Tracking dates can alert users to when infusate is no longer safe to use and replacement is required. Tracking infusate volume enables better and more precise planning of infusion delivery and timing of replacements. While transferring these types of information is discussed in relation to RFID technology, similar information could also be conveyed using one or more of the other technologies for sensing devices 860 or 860A discussed in this document.

Detection based on Near Field Communications (NFC) is another way to use appropriate sensing devices 860A on the pump and identifier 861A on the assembly 200A to provide a low power option for identification.

In certain embodiments, the information acquired via the sensing device 860A will be utilized for auto programming (or "smart pump programming") of the pump 800. Auto programming can help eliminate infusion errors and provide more prompt and timely patient care. In some auto programming embodiments, a manual override of programming is provided as well for patient safety.

In some cases, the identification sensor 860A may be color sensor 860 that relies on sensing visible light and/or infrared (IR) light. A color sensor 860 can use an IR channel for detection of IR properties of the assembly 200. By relying on an IR channel for identification, the sensor 860 can detect variations in color of an assembly 200 that are not readily visible to users. Accordingly, use of the IR channel may help deter or prevent unauthorized assemblies 200 from being used as non-visible device authorization information can be more challenging to replicate by unauthorized manufacturers or suppliers of such assemblies 200.

Similarly, in some cases, a pump 800 could be programmed to recognize and respond to a very specific "Pantone" color or specific color range. In such an embodiment, the specific color could indicate a route of infusion, or provide a virtual key to prevent use of unauthorized assemblies 200, or provide a combination of both an indication of route of infusion and a virtual key to prevent use of unauthorized assemblies 200. For example, an unauthorized assembly 200 without the right Pantone color or specific color range as an identifier 861A would not work in the pump 800. In general, the various identification sensors 860A, including various forms of color sensor 860, can prevent an assembly 200 from working with a pump 200 if the proper authentication information is not detected. Authentication features which restrict the use of assemblies 200 can vary significantly and are not limited by the types of authentication specifically disclosed herein.

In some embodiments, the identifier 861A on the assembly 200 or 200A is a colored label or other adhereable or insertable, permanent or temporary, identifying tag. In other embodiments the color, or identifier 861A is part of or integral to the frame or structure of the assembly 200 or 200A. The location of the identifier 861A may vary on the frame of assembly 200 or 200A. Likewise, the location of the sensing device 860A may vary within the assembly receptacle 812A of the infusion pump 800A.

As shown in FIG. 13, a reference/calibration portion 864A can be included in or on door 816A of the pump 800A in some embodiments. The reference/calibration portion 864A can be configured to be in close proximity or generally adjacent the sensing device 860A when door 816A is closed and assembly 200A is not received by assembly receptacle 812A. In some cases, the reference/calibration portion 864A may be a self-test label which causes the pump to signal a need for or otherwise prompt a self-test, whether automatic or manually-initiated, when no assembly 200A is inserted to obstruct or otherwise prevent the sensing device from reading the self-test label of the portion 864A.

Specifically, a self-test label, such as reference/calibration portion 864A, may identify a "no disposable condition" or "no assembly condition" when no assembly 200A is inserted in assembly receptacle 812A. This may be a label displaying a particular color that is capable of being optically sensed, for example. Other types of "no disposable condition" or "no assembly condition" labels or components are possible as well. Therefore, the pump 800A can readily and immediately detect when no disposable is installed and operate accordingly. By this feature, the pump 800A has a greater awareness of its current configuration and capabilities.

In certain embodiments, such as those relying upon a color on the assembly 200 or 200A to convey infusion "route" or other identification information, the color may further be recognized by the pump and automatically implemented as the background color in the pump graphic user interface (GUI). The consistent use of color for a particular "route" or other identification grouping can provide an intuitive and user-friendly control for a user. This type of consistency can help minimize or avoid user mistakes and human error.

Persons of ordinary skill in arts relevant to this disclosure and subject matter hereof will recognize that embodiments may comprise fewer features than illustrated in any individual embodiment described by example or otherwise contemplated herein. Embodiments described by example or otherwise contemplated herein are not meant to be an exhaustive presentation of ways in which various features may be combined and/or arranged. Accordingly, the embodiments are not mutually exclusive combinations of features; rather, embodiments can comprise a combination of different individual features selected from different individual embodiments, as understood by persons of ordinary skill in the relevant arts. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of Section 112 (f) of 35 U.S.C. are not to be invoked unless the specific terms "means for" or "step for" are recited in a claim.

What is claimed is:

1. An assembly configured to position a peristaltic tube with respect to a linear peristaltic pump drive of an infusion pump, the assembly comprising:
   a frame, configured to be releasably coupled to the infusion pump such that the peristaltic tube is placed in contact with the linear peristaltic pump drive;
   a first tube coupler and a second tube coupler, each configured to be connected to opposing ends of the peristaltic tube and each having a lumen in fluidic communication with the peristaltic tube, wherein the frame is fixedly coupled to both the first tube coupler and the second tube coupler;
   a free-flow prevention arm hingedly coupled to the frame and having a latching structure configured to cooperate with a latching receiver of the frame, the latching structure including a thumb press surface oppositely-disposed of the latching receiver and a release catch offset a distance from the thumb press surface, the free-flow prevention arm configured to alternate between a closed position and an open position by pivoting in a direction that is substantially perpendicular to a longitudinal axis of the peristaltic tube such that the release catch is configured to grip a latching surface of the latching receiver, wherein in the closed position the free-flow prevention arm and the frame compressively occlude the peristaltic tube, and in the open position the free-flow prevention arm and the frame allow the peristaltic tube to pass therebetween such that the peristaltic tube is not occluded; and
   a biasing mechanism located between the frame and the free-flow prevention arm, the biasing mechanism configured to bias the free-flow prevention arm to the closed position.

2. The assembly of claim 1, wherein the latching receiver of the frame includes a finger press surface.

3. The assembly of claim 1, wherein the release catch of the latching structure of the free-flow prevention arm is structured to provide a surface for a human finger to flex the free-flow prevention arm sufficiently to unlatch a latching mechanism provided by the latching structure and the latching receiver.

4. The assembly of claim 1, wherein the release catch of the latching structure of the free-flow prevention arm is structured to cooperate with at least one ramp in an assembly receptacle of the infusion pump so that when the assembly is secured to the assembly receptacle, the release catch slides along the at least one ramp as the free-flow prevention arm is moved toward the open position, such that force exerted on the release catch by the at least one ramp flexes the free-flow prevention arm sufficiently to prevent a latching mechanism provided by the latching structure and the latching receiver from latching in the open position.

5. The assembly of claim 1, wherein the release catch of the latching structure of the free-flow prevention arm is structured to cooperate with at least one ramp in an assembly receptacle of the infusion pump such that if, before the assembly is secured to the assembly receptacle, a latching mechanism provided by the latching structure and the latching receiver is latched in the open position, then subsequently when the assembly is secured to the assembly receptacle via a snap-fit tab, the at least one ramp exerts force on the release catch adequate to flex the free-flow prevention arm sufficiently that the latching mechanism is released.

6. The assembly of claim 1, wherein the biasing mechanism includes a spring formed separately from the frame and from the free-flow protection arm, the spring being captured between the frame and the free-flow protection arm.

7. The assembly of claim 1, wherein the free-flow prevention arm is hingedly coupled to the frame at an arm end.

8. The assembly of claim 7, wherein the free-flow prevention arm is hingedly coupled to the frame at the arm end via a hinge mechanism that substantially does not impart torque between the free-flow prevention arm and the frame.

9. The assembly of claim 1, wherein a latching mechanism provided by the latching structure and the latching receiver is ergonomically manipulable with a single hand to latch the free-flow prevention arm in the open position.

10. The assembly of claim 1, wherein a latching mechanism provided by the latching structure and the latching receiver is ergonomically manipulable with a single hand to unlatch the free-flow prevention arm such that the biasing mechanism is able to bias the free-flow prevention arm to the closed position.

11. The assembly of claim 1, wherein the frame defines a slot transverse to the peristaltic tube and generally aligned with the free-flow prevention arm, such that when the free-flow prevention arm is in the closed position, the free-flow prevention arm presses the peristaltic tube at least partially into the slot.

12. The assembly of claim 11, wherein the frame includes a buttress spanning the slot, the buttress generally aligned with the peristaltic tube.

13. The assembly of claim 12, where the buttress provides a guard against accidental latching of a latching mechanism provided by the latching structure and the latching receiver.

14. The assembly of claim 1, wherein the frame includes a first beam and a second beam.

15. The assembly of claim 14, wherein at least one of the first and second beams is substantially L-shaped.

16. The assembly of claim 1, further comprising a first securement plate.

17. The assembly of claim 16, wherein the first securement plate includes an identifier containing information related to a route of infusion associated with the assembly.

18. The assembly of claim 17, wherein the identifier is a colored surface or tag providing an associated visible or infrared optical wavelength for detection.

19. The assembly of claim 17, wherein the identifier contains at least one of: an RFID tag, a magnetic key, an identifying pin configuration, and an identifying protrusion.

20. An assembly configured to position a peristaltic tube with respect to a linear peristaltic pump drive of an infusion pump, the assembly comprising:
a frame, configured to be releasably coupled to the infusion pump such that the peristaltic tube is placed in contact with the linear peristaltic pump drive;
a first tube coupler and a second tube coupler, each configured to be connected to opposing ends of the peristaltic tube and each having a lumen in fluidic communication with the peristaltic tube, wherein the frame is fixedly coupled to both the first tube coupler and the second tube coupler;
a free-flow prevention arm hingedly coupled to the frame and having a latching structure configured to cooperate with a latching receiver of the frame, the latching structure including a thumb press surface oppositely-disposed of the latching receiver and a release catch offset a distance from the thumb press surface, the free-flow prevention arm configured to alternate between a closed position and an open position by pivoting in a direction that is substantially perpendicular to a longitudinal axis of the frame such that the release catch is configured to grip a latching surface of the latching receiver, wherein in the closed position the free-flow prevention arm and the frame compressively occlude the peristaltic tube, and in the open position the free-flow prevention arm and the frame allow the peristaltic tube to pass therebetween such that the peristaltic tube is not occluded; and
a biasing mechanism located between the frame and the free-flow prevention arm, the biasing mechanism configured to bias the free-flow prevention arm to the closed position.

* * * * *